United States Patent
Liu et al.

(10) Patent No.: US 12,090,216 B2
(45) Date of Patent: Sep. 17, 2024

(54) PEELABLE MAKEUP REMOVING COMPOSITIONS

(71) Applicant: L'OREAL, Paris (FR)

(72) Inventors: Tianyi Liu, Austin, TX (US); Koji Endo, Kawasaki (JP); Prabhjot K. Saini, Fanwood, NJ (US)

(73) Assignee: L'OREAL, Paris (FR)

( * ) Notice: Subject to any disclaimer, the term of this patent is extended or adjusted under 35 U.S.C. 154(b) by 27 days.

(21) Appl. No.: 17/494,227

(22) Filed: Oct. 5, 2021

(65) Prior Publication Data

US 2023/0108556 A1   Apr. 6, 2023

(51) Int. Cl.
| | |
|---|---|
| *A61K 8/02* | (2006.01) |
| *A61K 8/06* | (2006.01) |
| *A61K 8/81* | (2006.01) |
| *A61K 8/92* | (2006.01) |
| *A61Q 1/14* | (2006.01) |

(52) U.S. Cl.
CPC ............ *A61K 8/0212* (2013.01); *A61K 8/064* (2013.01); *A61K 8/8152* (2013.01); *A61K 8/92* (2013.01); *A61Q 1/14* (2013.01); *A61K 2800/31* (2013.01); *A61K 2800/95* (2013.01)

(58) Field of Classification Search
None
See application file for complete search history.

(56) References Cited

U.S. PATENT DOCUMENTS

| 5,747,022 | A | 5/1998 | Slavtcheff |
| 9,949,897 | B2 | 4/2018 | Shiroya et al. |
| 2006/0159730 | A1 | 7/2006 | Simon |
| 2007/0110792 | A9 | 5/2007 | Simon |
| 2007/0248633 | A1 | 10/2007 | Baldo |
| 2009/0022700 | A1 | 1/2009 | Cassin et al. |
| 2009/0269377 | A1 | 10/2009 | Lu |
| 2009/0317432 | A1 | 12/2009 | Kergosien |
| 2010/0080766 | A1 | 4/2010 | Dumousseaux et al. |
| 2011/0033509 | A1 | 2/2011 | Simon |
| 2011/0165102 | A1 | 7/2011 | Arditty et al. |
| 2012/0156270 | A1 | 6/2012 | Cassin et al. |
| 2013/0048004 | A1* | 2/2013 | Wei .............. A45D 40/26 206/524.1 |
| 2013/0167859 | A1 | 7/2013 | Bui et al. |
| 2020/0187624 | A1 | 6/2020 | Truong |
| 2020/0188707 | A1 | 6/2020 | Truong |
| 2020/0315319 | A1 | 10/2020 | Samain |

FOREIGN PATENT DOCUMENTS

| FR | 2834916 A1 | 7/2003 |
| FR | 2862869 A1 | 6/2005 |

OTHER PUBLICATIONS

BASF "Kolliphor RH 40" <https://pharma.basf.com/technicalinformation/30555082/kolliphor-rh-40> available Jan. 2020; accessed Jun. 15, 2023 (Year: 2020).*
Deckner, George. "An Overview of Emollient Technology" <https://www.ulprospector.com/knowledge/5840/pcc-emollient-technology-overview/> (Year: 2017).*
Preliminary Search Report and Written Opinion issued on Aug. 8, 2022, for corresponding French Application No. FR 2113545.

* cited by examiner

*Primary Examiner* — Nicole P Babson
(74) *Attorney, Agent, or Firm* — POLSINELLI PC

(57) ABSTRACT

Disclosed are compositions, such as makeup removing compositions, that can form a film on a keratin material, such as skin that lifts and removes makeup from the keratin material, such as skin. The compositions may be an aqueous composition including: (a) a hydrophobically modified acrylate film forming homopolymer or copolymer; (b) a hydrophilic film forming polymer; (c) a volatile oil; (d) a nonionic surfactant; (e) optionally, a monoalcohol having from 2 to 5 carbon atoms; and (f) water. Alternatively, the compositions may be anhydrous compositions including: (a) a hydrophobically modified acrylate film forming homopolymer or copolymer; (b) a plasticizer; and (c) a volatile oil. Also disclosed are methods for cleansing and removing makeup from keratin material, such as skin.

11 Claims, No Drawings

PEELABLE MAKEUP REMOVING COMPOSITIONS

FIELD OF THE DISCLOSURE

The instant disclosure relates to makeup removing compositions that can form films. The films adhere to makeup on the skin, which is efficiently and easily removed when the films are removed (or peeled) from the skin. Also disclosed are methods for using the makeup removing compositions for removing makeup and cleansing the skin.

BACKGROUND

Removal of makeup from the skin is very important for facial care. Fatty residues from excess sebum and from cosmetic products accumulate on the skin. These accumulations can block skin pores and cause the appearance of objectionable spots. Nonetheless, consumers seek makeup products having increasingly long persistence, for example, waterproof mascaras, long-lasting and transfer-resistant foundations, and lipsticks that last all day. Long-lasting mascaras typically have high amounts of film-forming polymers dispersed either in aqueous phase or in anhydrous phase. These dispersed film-forming polymers improve persistence and provide rub resistance.

Cosmetic products incorporating dispersed polymers tend to be difficult to remove from the skin. Removing these products are difficult and require harsh cleansers that tend to irritate and dry the skin. Therefore, oil-based makeup removers have been developed that target waterproof makeup products. However, some long-wear products include high amounts of certain polymers, such as styrene acrylate, upon which oil-based products have little effect. These long-wear products tend to be resistant to water, detergent-based cleansers, and oil-based makeup removers.

Product in the form of emulsion exist containing large amounts of oil, which provides makeup-removing effectiveness. However, these products typically result in an unpleasant and unsightly greasiness on the skin. On the other hand, aqueous makeup-removing products that include surfactants and little or no oil require intense scrubbing. The surfactants provide cleansing properties to the products but can irritate and dry the skin.

There remains a need for both aqueous and anhydrous makeup-removing products that are efficient, gentle to the skin, and easy to use. Such products should easily remove all types of makeup including products containing high amounts of film-forming polymers. Accordingly, it would be beneficial to provide a cleansing product for the skin that efficiently removes makeup and addresses the needs described above.

SUMMARY OF THE DISCLOSURE

The makeup removing compositions of the instant disclosure are unique in their ability to form a makeup removing film on the skin. Unlike traditional makeup removers that require scrubbing and rinsing from the skin, the films can be peeled from the skin. The makeup on the skin adheres to the film and is lifted from the skin with removal of the films. It was discovered the hydrophobically modified acrylate film forming copolymers are useful in both aqueous and anhydrous makeup removing compositions. The hydrophobically modified acrylate film forming copolymer can be combined with a hydrophilic film forming polymer in aqueous compositions in the form of a water-in-oil emulsion. For anhydrous compositions, the hydrophobically modified acrylate film forming copolymer is combined with a plasticizer. These combinations provide the makeup removing compositions with surprising film-forming and makeup removing properties.

Thus, an object of the invention is a cosmetic composition, especially a makeup composition, particularly a makeup removing composition, preferably in the form of a water-in-oil emulsion and typically include:
 (a) about 15 to about 55 wt. % of a hydrophobically modified acrylate film forming homopolymer or copolymer, preferably copolymer;
 (b) a hydrophilic film forming polymer;
 (c) a volatile oil;
 (d) a nonionic surfactant;
 (e) optionally, a monoalcohol having from 2 to 5 carbon atoms; and
 (f) water,
  wherein the composition is a water-in-oil emulsion, and all weight percentages are based on the total weight of the composition.

Another object of the invention is a composition, preferably an anhydrous makeup composition, preferably a makeup removing composition typically including:
 (a) about 15 to about 55 wt. % of a hydrophobically modified acrylate film forming homopolymer or copolymer, preferably copolymer;
 (b) a plasticizer; and
 (c) a volatile oil,
  wherein all weight percentages are based on the total weight of the composition.

Nonlimiting examples of useful hydrophobically modified acrylate film forming copolymers include acrylates/beheneth-25 methacrylate copolymer, acrylates/C10-30 alkyl acrylate crosspolymer, acrylates/ceteth-20 itaconate copolymer, acrylates/ceteth-20 methacrylate copolymer, acrylates/laureth-25 methacrylate copolymer, acrylates/palmeth-20 acrylate copolymer, acrylates/palmeth-25 acrylate copolymer, acrylates/palmeth-25 itaconate copolymer, acrylates/steareth-50 acrylate copolymer, acrylates/steareth-20 itaconate copolymer, acrylates/steareth-20 methacrylate copolymer, acrylates/stearyl methacrylate copolymer, acrylates/vinyl isodecanoate crosspolymer, acrylates/steareth-20 methacrylate crosspolymer, octylacrylamide/acrylates/butylaminoethyl methacrylates copolymer, acrylates/C12-alkylmethacrylate copolymer, acrylates/steareth (or ceteth)-20 itaconate copolymer, steareth-10 allyl ether/acrylate copolymer, acrylates/vinyl acetate crosspolymer, glyceryl polymethacrylate, ammonium acryloyldimethyltaurate/beheneth-25 methacrylate copolymer, and a mixture thereof. A particularly useful hydrophobically modified acrylate film forming copolymer is acrylates/stearyl methacrylate copolymer.

Nonlimiting examples of hydrophilic film forming polymers include polyurethanes, vinyl polymers, natural polymers, copolymers derived from $C_4$-$C_8$ monounsaturated carboxylic acids or anhydrides, methyl vinyl ether/butyl monomaleate copolymers, polysaccharides, guar gums and modified guar gums, celluloses, gellan gum and derivatives thereof, acrylate and methacrylate copolymers, polyvinyl pyrollidone, polyvinyl alcohol, polyvinyl acetate, water soluble gums, water soluble celluloses, dextrans, hyaluronic acid, cyclodextrins, polysaccharide polymers, polyvinyl caprolactam-polyvinyl acetate-polyethylene glycol graft copolymers, and mixtures thereof. Particularly useful hydrophilic film forming polymers include polyvinyl pyrollidone, polyvinyl alcohol, polyvinyl acetate, and mixtures thereof.

The volatile oil may include hydrocarbon oils, silicone oils, ester oils, and mixtures thereof. In some cases, however, hydrocarbon oils are particularly useful, for example, isoparaffin, isohexadecane, isododecane, isodecane, undecane, tridecane, dodecane, isohexyl, isodecyl, neopentanoate, and mixtures thereof.

Nonlimiting examples of nonionic surfactants include alkyl polyglucosides; alcohols, alpha-diols, alkylphenols and esters of fatty acids, being ethoxylated, propoxylated or glycerolated; ethoxylated fatty esters; glyceryl esters of fatty acids; fatty alcohol ethoxylates; alkyl phenol ethoxylates; fatty acid alkoxylates; and mixtures thereof. In some cases, polyglycerolated esters of fatty acids (e.g., C12-C18 fatty acids), are particularly useful.

Non-limiting examples of monoalcohols having from 2 to 5 carbon atoms include methanol, ethanol, isopropyl alcohol, propanol, butanol, pentanol, and mixtures thereof.

The term "plasticizer" or "plasticizing agent" means an organic chemical compound, which is in solid state or in liquid state, at room temperature and at atmospheric pressure, and which is added to a composition comprising different types of polymerizable ingredients (monomers) to make the polymer more supple, more flexible, and/or to improve its mechanical strength. Plasticizers are known to those skilled in the art; mention may be made, for example, of "Plasticizers", *Encyclopedia of polymer Science and Technology*, Helmut Reinecke, Rodrigo Navarro, Mónica Pérez, https://doi.org/10.1002/0471440264.pst245.pub215 September 2011.

For the purposes of the invention, the plasticizers have a molecular weight of between 150 and 1000 g/mol, particularly between 180 and 700, preferably between 200 and 600. The agents are also organic compounds consisting of carbon and hydrogen atoms and of one or more heteroatoms chosen from oxygen, sulfur and silicon atoms, in particular chosen from oxygen and silicon atoms, preferably at least 3 heteroatoms, even more preferentially between 4 and 10 heteroatoms, and which may contain one or more aryl groups such as benzyl. In particular, they comprise one or more groups chosen from esters, phthalate, benzoate, sulfonate, and citrates.

Preferably, the plasticizer(s) of the invention are chosen from those of the phthalate, ester, citrate, and benzoate families.

According to a particular embodiment of the invention, the plasticizer(s) are chosen from compounds (V) below:

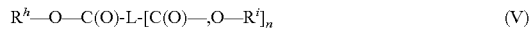
$$R^h\text{—O—C(O)-L-[C(O)—,O—}R^i]_n \qquad (V)$$

in which formula (V):
- $R^h$ and $R^i$, which may be identical or different, represent a group from among: $(C_1\text{-}C_{20})$alkyl, aryl such as phenyl, aryl$(C_1\text{-}C_4)$alkyl such as benzyl, preferably $(C_1\text{-}C_4)$alkyl such as n-butyl;
- n is 1, 2 or 3, preferably 2; and
- L represents a group from among: a) divalent, trivalent or tetravalent $C_1\text{-}C_{10}$ alkyl, preferably trivalent $(C_2\text{-}C_8)$ alkyl, said divalent, trivalent or tetravalent alkyl possibly being optionally substituted with one or more hydroxyl groups, b) divalent or trivalent cycloalkyl, or c) divalent, trivalent or tetravalent aryl, preferably divalent or trivalent phenyl; preferably, L represents a group a);

According to a particular embodiment of the invention, the compounds of formula (V) are chosen from the compounds of formula (V'):

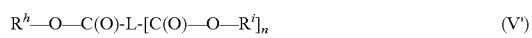
$$R^h\text{—O—C(O)-L-[C(O)—O—}R^i]_n \qquad (V')$$

in which formula (V):
- $R^h$ and $R^i$, which may be identical or different, represent a group from among: $(C_1\text{-}C_6)$alkyl, aryl$(C_1\text{-}C_4)$alkyl such as benzyl, preferably $(C_1\text{-}C_4)$alkyl such as n-butyl;
- n is 1 or 2, preferably 2; and
- L represents a group from among: a) divalent, trivalent or tetravalent $C_2\text{-}C_6$ alkyl, preferably trivalent $(C_2\text{-}C_8)$ alkyl, said alkyl possibly being optionally substituted with one or more hydroxyl groups, preferably substituted with a hydroxyl group.

Nonlimiting examples of plasticizers include phthalate plasticizers, terephthalate plasticizers, benzoate plasticizers, citrate plasticizers, phosphate plasticizers, adipate plasticizers, and mixtures thereof. More specific but nonlimiting examples include acetyl tributyl citrate, acetyl triethyl citrate, tributyl citrate, triethyl citrate, dibutyl phthalate, triphenylphosphate, triacetin, trimethyl pentanyl diisobutyrate, triethylhexanoin, sucrose benzoate, dibutyl adipate, diethyl phthalate, diisobutyl adipate, diisopropyl adipate, dipropylene glycol dibenzoate, N-ethyl toluene sulfonamide, ortho- and para-isomers of N-ethyl toluene sulfonamide, N-(2-hydroxypropyl) benzene sulfonamide, N-(n-butyl) benzene sulfonamide, and combinations thereof. In some cases, particularly useful plasticizers include citrate plasticizers, for example, acetyl tributyl citrate, acetyl triethyl citrate, tributyl citrate, triethyl citrate, and mixtures thereof.

According to a particular embodiment of the invention, the plasticizer(s) are in an amount of about 0.5% to about 15%, especially in an amount of about 1% to about 10%, preferably an amount of about 2 to about 7 wt. %, based on the total weight of the composition.

The instant disclosure also relates to methods for removing makeup from keratin material, especially the skin and/or methods of cleansing keratin material such as the skin. Such methods typically include:
(i) applying the composition, especially the makeup removing composition of the instant disclosure to the keratin material such as the skin;
(ii) allowing the composition to remain on the keratin material such as the skin for a period; and
(iii) removing the composition from the keratin material, such as the skin.

A unique property of the makeup removing compositions is their ability to form a film on the keratin material, such as the skin. The film forms on the keratin material, especially skin, quickly, for example, within 15, 10, or 5 minutes; and the film adheres to makeup on the keratin material such as skin. When the film is removed, the makeup attached to the film separates from the keratin material such as skin, leaving the keratin material, such as skin clean, e.g., the skin is free or essentially free from makeup. The film on the keratin material such as skin can be removed by peeling the film from the keratin material such as skin or can be removed by other means such as scrubbing and/or rinsing. If desired, the film formed on the keratin material (e.g., skin) can be removed in one piece but is not required to be removed in one piece. The makeup removing compositions are therefore useful for treating keratin materials such as skin, in particular the skin of the face. The makeup removing compositions can be used as a facial wash and/or as a makeup remover, as the products are particularly effective at cleansing the keratin material, including skin.

DETAILED DESCRIPTION OF THE DISCLOSURE

The makeup removing compositions of the instant disclosure containing hydrophobically modified acrylate film forming copolymers can be aqueous or anhydrous. The hydrophobically modified acrylate film forming copolymers are combined with a hydrophilic film forming polymer in aqueous compositions in the form of a water-in-oil emulsion. For anhydrous compositions, the hydrophobically modified acrylate film forming copolymers is combined with a plasticizer. These combinations provide the makeup compositions with surprising film-forming and makeup removing ability.

For the purposes of the present invention and unless otherwise indicated:

an "alkyl radical" is a linear or branched saturated hydrocarbon-based group, particularly $C_1$-$C_8$, more particularly $C_1$-$C_6$, preferably $C_1$-$C_4$ such as methyl, ethyl, isopropyl and tert-butyl;

an "alkoxy radical" is a alkyl-oxy wherein alkyl is as described herein before;

an "alkenyl radical" is a linear or branched unsaturated hydrocarbon-based group, particularly $C_2$-$C_8$, more particularly $C_2$-$C_6$, preferably $C_2$-$C_4$ such as ethylenyl, propylenyl;

an "alkylene radical" is a linear or branched divalent saturated $C_1$-$C_8$, in particular $C_1$-$C_6$, preferably $C_1$-$C_4$ hydrocarbon-based group such as methylene, ethylene or propylene.

The compositions of the invention, especially aqueous compositions, preferably for makeup, more preferably for makeup removing compositions are preferably in the form of a water-in-oil emulsion and typically include:

(a) about 15 to about 55 wt. % of a hydrophobically modified acrylate film forming homopolymers or copolymers, preferably copolymers;
(b) about 1 to about 25 wt. % of a hydrophilic film forming polymer;
(c) about 30 to about 75 wt. % of a volatile oil;
(d) 0.01 to about 10 wt. % of a nonionic surfactant;
(e) 0.1 to about 25 wt. % of a monoalcohol having from 2 to 5 carbon atoms; and
(f) about 5 to about 45 wt. % of water;
wherein all weight percentages are based on the total weight of the composition.

The anhydrous compositions, preferably the anhydrous makeup removing compositions typically contain 2 wt. % or less of water and:

(a) about 10 to about 60 wt. % of a hydrophobically modified acrylate film forming copolymer;
(b) about 0.5 to about 15 wt. % of a plasticizer; and
(c) about 30 to about 75 wt. % of a volatile oil,
all weight percentages are based on the total weight of the composition.

Hydrophobically Modified Acrylate Film Forming Homopolymers and Copolymers

The solubility of the "hydrophobically modified" homopolymers or copolymers mean they can be dispersible in oil and have no or limited affinity for water at 25° C. and at atmospheric pressure (760 mmHg), is preferably less than 0.05% by weight, and preferably less than 0.01%.

The term "hydrophilic film forming polymer" is interchangeable with the term "water-miscible solvent" and means a compound that is liquid at 25° C. and at atmospheric pressure (760 mmHg), and it has a solubility of at least 50% in water under these conditions.

Nonlimiting examples of useful hydrophobically modified acrylate film forming homopolymers include beheneth-25 methacrylate polymer, $C_{10}$-$C_{30}$ alkyl acrylate crosspolymer, ceteth-20 itaconate polymer, ceteth-20 methacrylate polymer, laureth-25 methacrylate polymer, palmeth-20 acrylate polymer, palmeth-25 acrylate polymer, palmeth-25 itaconate polymer, steareth-50 acrylate polymer, steareth-20 itaconate polymer, steareth-20 methacrylate polymer, stearyl methacrylate polymer, vinyl isodecanoate crosspolymer, steareth-20 methacrylate crosspolymer, C12-alkylmethacrylate polymer, steareth (or ceteth)-20 itaconate polymer steareth-10 allyl ether/acrylate polymer, vinyl acetate crosspolymer, and a mixture thereof. A particularly useful hydrophobically modified acrylate film forming homopolymer is stearyl methacrylate homopolymer.

The hydrophobically-modified acrylate film forming copolymers are copolymers formed from segments with different hydrophobicity which are oil soluble and oil insoluble. As the term "hydrophobically-modified" denotes, they can be dispersible in oil and have no or limited affinity for water.

The hydrophobically-modified acrylate film forming copolymers are often provided in an oily dispersion. Such dispersions may be obtained by polymerizing particular monomers that are capable of forming a polymeric core i) in the presence of a polymeric statistical stabilizer ii) comprising in major amount a part ii) that is soluble and in minor amount a part i) that is insoluble in the dispersion medium, i.e. in the hydrocarbon-based liquid fatty substance(s). The dispersions thus consist of particles, which are generally spherical, and of at least one surface-stabilized polymer, in an anhydrous medium. Preferably, the particles i) are not or are sparingly crosslinked.

Polymer Particles i)

The particle(s) of the oily dispersion preferably consist of one or more polymers chosen from:

a) ethylenic homopolymers of ($C_1$-$C_4$)alkyl ($C_1$-$C_4$)(alkyl)acrylate, preferably ($C_1$-$C_4$)alkyl (meth)acrylate ethylenic homopolymers;
b) ethylenic copolymers of ($C_1$-$C_4$)alkyl ($C_1$-$C_4$)(alkyl)acrylate, preferably ($C_1$-$C_4$)alkyl (meth)acrylate, and of ($C_1$-$C_4$)(alkyl)acrylic acid, preferably (meth)acrylic acid ethylenic copolymers;
c) ethylenic copolymers of ($C_1$-$C_4$)alkyl ($C_1$-$C_4$)(alkyl)acrylate, preferably ($C_1$-$C_4$)alkyl (meth)acrylate ethylenic copolymers; and Preferably, the particle(s) i) consist of an ethylenic polymeric core derived from homopolymers a) or copolymers b) or c) as defined previously.

According to a preferred embodiment of the invention, the polymer constituting the particles i) is an ethylenic acrylate homopolymer a) resulting from the polymerization of an identical monomer of formula (I):

$$H_2C=C(R)-C(O)-O-R' \quad (I)$$

in which formula (I):
R represents a hydrogen atom or a ($C_1$-$C_4$)alkyl group such as methyl, and
R' represents a ($C_1$-$C_4$)alkyl group such as methyl or ethyl, preferably monomer of formula (I) is a $C_1$-$C_4$ alkyl acrylate such as methyl acrylate.

According to a particular embodiment, the polymer constituting the particles i) is an ethylenic acrylate copolymer b) resulting from the polymerization:
of at least one monomer of formula (I) as defined previously, preferably a $C_1$-$C_4$ alkyl acrylate such as methyl acrylate and ethyl acrylate; and
of a monomer of formula (II)

$$H_2C=C(R)-C(O)-O-H \quad (II)$$

in which formula (II) R is as defined previously, in particular monomer of formula (II) is acrylic acid.

According to this embodiment, the amount of acrylic acid ranges from 0.1% to 15% by weight relative to the weight of monomers of the particle i) and the polymer of the particles i) is in particular a copolymer derived from the copolymerization of acrylic acid with one or more $C_1$-$C_4$ alkyl (meth)acrylate monomers chosen in particular from methyl (meth)acrylate and ethyl (meth)acrylate.

According to another preferred embodiment, the polymer constituting the particles i) is an ethylenic acrylate copolymer b) derived from the polymerization:
- of at least two different monomers: of formula (I) as defined previously, preferably a $C_1$-$C_4$ alkyl acrylate such as methyl acrylate and ethyl acrylate; and
- optionally of a monomer of formula (II) as defined previously.

[According to a particular embodiment, the polymer of the particles i) is a polymer derived from $C_1$-$C_4$ alkyl (meth)acrylate monomers. The monomers are preferably chosen from methyl (meth)acrylate, ethyl (meth)acrylate, n-propyl (meth)acrylate, isopropyl (meth)acrylate, n-butyl (meth)acrylate and tert-butyl (meth)acrylate, and more preferentially chosen from methyl (meth)acrylate and ethyl (meth)acrylate.

Advantageously, a $C_1$-$C_4$ alkyl acrylate monomer is used. Preferentially, the monomers are chosen from methyl acrylate and ethyl acrylate.

A $C_1$-$C_4$ alkyl methacrylate monomer is also particularly used. Preferentially, the monomers are chosen from methyl methacrylate and ethyl methacrylate, more particularly methyl methacrylate.

According to a particular embodiment of the invention, the oily dispersion includes from 2% to 40% by weight, in particular 4% to 25%, notably from 5% to 20% by weight of ($C_9$-$C_{22}$)alkyl ($C_1$-$C_6$)(alkyl)acrylate monomers included in d) or e) in the hydrocarbon-based liquid fatty substance(s) iii), relative to the total weight of polymers contained in said dispersion.

According to an advantageous embodiment of the invention, the oily dispersion includes from 60% to 98% by weight, notably from 75% to 96% of monomers a) to c) relative to the total weight of polymers contained in said dispersion.

Preferably, the monomers that are capable of forming the polymeric core of the particle i) are chosen from monomers that are insoluble in the hydrocarbon-based liquid fatty substance(s) iii) of the dispersion. The insoluble monomers preferably represent 100% by weight, relative to the total weight of the monomers forming the polymeric core of the particle.

According to one embodiment, the particles i) include b) ethylenic copolymers of b1) ($C_1$-$C_4$)alkyl ($C_1$-$C_4$)(alkyl) acrylate and of b2) ethylenic monomers comprising one or more carboxyl, anhydride, phosphoric acid, sulfonic acid and/or aryl groups such as benzyl.

More particularly, the ethylenic monomers comprising one or more carboxyl, anhydride, phosphoric acid, sulfonic acid and/or aryl groups are chosen from (1), (2), (3), (4) and (5):

(1) $R^1(R^2)C=C(R^3)$-Acid with $R^1$, $R^2$ and $R^3$ representing a hydrogen atom or a $CO_2H$, $H_2PO_4$ or $SO_3H$ group, and Acid representing a carboxyl, phosphoric acid or sulfonic acid, preferably carboxyl, it being understood that $R^1$, $R^2$ and $R^3$ cannot simultaneously represent a hydrogen atom;

(2) $H_2C=C(R)-C(O)-N(R')$-Alk-Acid with R and R', which may be identical or different, representing a hydrogen atom or a ($C_1$-$C_4$)alkyl group; Alk represents a ($C_1$-$C_6$)alkylene group optionally substituted with at least one group chosen from Acid as defined previously and hydroxyl; and Acid is as defined previously, preferably carboxyl or sulfonic acid;

(3) Ar—$(R^a)C=C(R^b)$—$R^c$ with $R^a$, $R^b$ and $R^c$, which may be identical or different, representing a hydrogen atom or a ($C_1$-$C_4$)alkyl group, and Ar representing an aryl group, preferably benzyl, optionally substituted with at least one acid group $CO_2H$, $H_2PO_4$, or $SO_3H$, preferably substituted with a $CO_2H$ or $SO_3H$ group, (4) maleic anhydride of formulae (4a) and (4b):

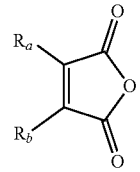

(4a)

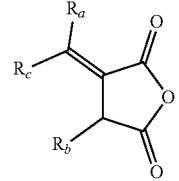

(4b)

in which formulae (4a) and (4b) $R_a$, $R_b$ and $R_c$, which may be identical or different, represent a hydrogen atom or a ($C_1$-$C_4$)alkyl group; preferably, $R_a$, $R_b$, and $R_c$ represent a hydrogen atom. Preferentially, the ethylenically unsaturated anhydride monomer of the invention is of formula (4b) and more preferentially is maleic anhydride; and (5) $H_2C=C(R)-C(O)-O-H$ with R representing a hydrogen atom or a ($C_1$-$C_4$)alkyl group such as methyl.

Preferably, b2) is a ($C_1$-$C_4$)(alkyl)acrylic acid, more particularly b) is (are) copolymers of ($C_1$-$C_4$)alkyl (meth) acrylate and of (meth)acrylic acid.

More preferentially, b2) is chosen from crotonic acid, maleic acid, itaconic acid, fumaric acid, styrenesulfonic acid, vinylbenzoic acid, vinylphosphoric acid, acrylic acid, methacrylic acid, acrylamidopropanesulfonic acid, acrylamidoglycolic acid and salts thereof; even more preferentially, b2) represents acrylic acid.

The polymer particles i) of the dispersion preferably have a number-mean size ranging from 5 to 500 nm, notably ranging from 10 to 400 nm and better still ranging from 20 to 300 nm.

The final particle size is preferably greater than 100 nm. In particular, the number-mean size ranges from 100 nm to 500 nm, more particularly ranges from 150 nm to 400 nm and even more particularly ranges from 160 nm to 300 nm.

The mean particle size is determined via standard methods known to those skilled in the art. A Malvern brand NanoZS model laser particle size analyser (which is particularly suitable for submicron dispersions) makes it possible to measure the size distribution of these samples. The operating principle of this type of machine is based on dynamic light scattering (DLS), also known as quasi-elastic light scattering (QELS) or photon correlation spectroscopy (PCS).

The sample is projected into a disposable plastic cuvette (four transparent faces, side length of 1 cm and volume of 4 mL) placed in the measuring cell. The data are analysed on the basis of a cumulative method which leads to a unimodal particle size distribution characterized by an intensity-mean diameter d (nm) and a size polydispersity factor Q. The results may also be expressed in the form of statistical data such as D10, D50 (median), D90 and mode.

Other particle size techniques make it possible to obtain this type of information, such as analysis of the individual tracking of particles (Nanoparticle Tracking Analysis, NTA), laser scattering (LS), acoustic extinction spectroscopy (AES), spatial-filter Doppler velocimetry or image analysis.

The Stabilizer(s) ii)

The dispersion also comprises one or more stabilizers ii). Preferably, a single type of stabilizer ii) is used.

According to a particular embodiment, the stabilizer(s) ii) are chosen from d) ethylenic homopolymers of $(C_9-C_{22})$ alkyl $(C_1-C_6)$(alkyl)acrylate, in particular ethylenic homopolymers of $(C_9-C_{18})$alkyl $(C_1-C_4)$(alkyl)acrylate, preferably ethylenic homopolymers of $(C_9-C_{22})$alkyl (meth) acrylate and more preferentially ethylenic homopolymers of $(C_9-C_{18})$alkyl (meth)acrylate. Particularly the $(C_9-C_{22})$alkyl or the $(C_9-C_{18})$alkyl groups are linear. According to another variant of the invention the $(C_9-C_{22})$alkyl or the $(C_9-C_{18})$ alkyl groups are branched.

More particularly, the stabilizer(s) ii) consist of ethylenic polymers chosen from d) ethylenic homopolymers resulting from the polymerization of monomers of formula $H_2C=C(R)-C(O)-O-R''$ with R representing a hydrogen atom or a $(C_1-C_4)$alkyl group such as methyl, and R" representing a $(C_9-C_{22})$alkyl and preferably $(C_9-C_{18})$alkyl group. Preferably, R" represents isodecyl, lauryl, stearyl, hexadecyl or behenyl. According one embodiment of the invention R" represents a linear $(C_9-C_{22})$alkyl and preferably a linear $(C_9-C_{18})$alkyl group.

According to another particular embodiment, the stabilizer(s) ii) are chosen from e) ethylenic copolymers of $(C_9-C_{22})$alkyl $(C_1-C_6)$(alkyl)acrylate and of $(C_1-C_4)$alkyl $(C_1-C_4)$(alkyl)acrylate, particularly copolymers of $(C_9-C_{18})$ alkyl $(C_1-C_4)$(alkyl)acrylate and of $(C_1-C_4)$alkyl $(C_1-C_4)$ (alkyl)acrylate, preferably copolymers of $(C_9-C_{18})$alkyl (meth)acrylate and of $(C_1-C_4)$alkyl (meth)acrylate.

More preferentially, the stabilizer(s) ii) are chosen from the ethylenic copolymers e) of formulae (III) and (IV):

$$H_2C=C(R)-C(O)-O-R' \quad (III)$$

$$H_2C=C(R)-C(O)-O-R'' \quad (IV)$$

in which formulae (III) and (IV):
R, which may be identical or different, represent a hydrogen atom or a $(C_1-C_4)$alkyl group such as methyl,
R', which may be identical or different, represent a $(C_1-C_4)$alkyl group such as methyl or ethyl, and
R" represents a $(C_9-C_{22})$alkyl, preferably $(C_{10}-C_{20})$alkyl and in particular $(C_{2n})$alkyl group with n being an integer equal to 5, 6, 7, 8, 9 or 10. Preferably, R" represents isodecyl, lauryl, stearyl, hexadecyl or behenyl.

Preferentially, the stabilizer(s) ii) are chosen from copolymers derived from monomers chosen from isodecyl, lauryl, stearyl, hexadecyl and behenyl (meth)acrylates and $C_1-C_4$ alkyl (meth)acrylate, preferably methyl (meth)acrylate.

More preferentially, the stabilizer(s) ii) are chosen from copolymers derived from monomers chosen from isodecyl, lauryl, stearyl and hexadecyl (meth)acrylates and $C_1-C_4$ alkyl (meth)acrylate, preferably methyl (meth)acrylate or ethyl (meth)acrylate.

In particular, the stabilizer ii) is chosen from isodecyl, lauryl, stearyl, hexadecyl or behenyl (meth)acrylate homopolymer and statistical copolymers of isodecyl, lauryl, stearyl, hexadecyl or behenyl (meth)acrylate and of $C_1-C_4$ alkyl (meth)acrylate preferably present in a lauryl, stearyl, hexadecyl or behenyl (meth)acrylate/$C_1-C_4$ alkyl (meth) acrylate weight ratio of greater than 4.5.

Advantageously, said weight ratio ranges from 5 to 15 and more preferentially said weight ratio ranges from 5.5 to 12.

According to another embodiment, the stabilizer(s) ii) are chosen from ethylenic copolymers e) derived from the polymerization of a monomer of formula (IV) as defined previously and two different monomers of formula (III) as defined previously.

Preferentially, the stabilizer(s) ii) are chosen from copolymers derived from the polymerization of one monomer chosen from isodecyl, lauryl, stearyl, hexadecyl and behenyl (meth)acrylates and of two different $C_1-C_4$ alkyl (meth) acrylates, preferably methyl acrylate and ethyl acrylate. In particular, the weight ratio of isodecyl, lauryl, stearyl, hexadecyl or behenyl (meth)acrylates/$C_1-C_4$ alkyl (meth)acrylate is greater than 4. Advantageously, said weight ratio ranges from 5 to 15 and more preferentially said weight ratio ranges from 5.5 to 11.

According to another embodiment, the stabilizer(s) ii) are chosen from ethylenic copolymers e) derived from the polymerization of a monomer of formula (III) as defined in the preceding claim and two different monomers of formula (IV) as defined previously.

Preferentially, the stabilizer(s) ii) are chosen from copolymers derived from the polymerization of two different monomers chosen from isodecyl, lauryl, stearyl, hexadecyl and behenyl (meth)acrylates and of one $C_1-C_4$ alkyl (meth) acrylate monomer, preferably methyl acrylate and ethyl acrylate; in particular, the weight ratio of isodecyl, lauryl, stearyl, hexadecyl or behenyl (meth)acrylates/$C_1-C_4$ alkyl (meth)acrylate is greater than 4.

Advantageously, said weight ratio ranges from 4.5 to 10 and more preferentially said weight ratio ranges from 5 to 8.

According to a particular embodiment of the invention, the oily dispersion includes from 2% to 40% by weight, in particular 4% to 25%, notably from 5.5% to 20% by weight of $(C_9-C_{22})$alkyl $(C_1-C_6)$(alkyl)acrylate monomers included in d) or e) in the hydrocarbon-based liquid fatty substance(s) iii), relative to the total weight of polymers contained in said dispersion.

According to one embodiment, the stabilizer(s) ii) are chosen from copolymers derived from the polymerization of two different monomers chosen from isodecyl, lauryl, stearyl, hexadecyl and behenyl (meth)acrylates and of one $C_1-C_4$ alkyl (meth)acrylate monomer, preferably methyl acrylate and ethyl acrylate; in particular, the weight ratio of isodecyl, lauryl, stearyl, hexadecyl or behenyl (meth)acrylates/$C_1-C_4$ alkyl (meth)acrylate in the dispersion (A) is less than 1. Particularly, said weight ratio ranges from 0.05 to 0.5 and more preferentially said weight ratio ranges from 0.08 to 0.2 in the dispersion (A).

For these statistical copolymers, the defined weight ratio makes it possible to obtain a polymer dispersion that is stable, notably after storage for seven days at room temperature.

Advantageously, the weight ratio of ii) stabilizer(s) and i) of polymer particle(s) present in the dispersion (A) is between 0.5 and 2, preferably 1.

In particular, the weight ratio of ii) stabilizer(s) and i) polymer particle(s) is less than 1, relative to the total weight of polymers.

According to a particular embodiment, the stabilizer(s) ii) are present in a content ranging from 2% to 40% by weight, notably from 3% to 30% by weight and preferably from 4% to 25% by weight relative to the weight of polymer(s) present in the dispersion (A).

Preferably, the stabilizer(s) ii) and the particle(s) i) have a number-average molecular weight (Mn) of between 1000 and 1 000 000 g/mol, notably between 5000 and 500 000 g/mol and even better still between 10 000 and 300 000 g/mol.

The dispersion is finally formed from polymeric particles of relatively large diameter, i.e. preferably greater than 100 nm, and leads to glossy, film-forming deposits which are resistant to fatty substances at room temperature (25° C.), which are advantageously notably for makeup applications.

The Hydrocarbon-Based Liquid Fatty Substance(s) iii)

The dispersion of polymer particles also comprises iii) one or more hydrocarbon-based liquid fatty substances in which said particles are dispersed.

The hydrocarbon-based liquid fatty substances iii) are notably chosen from $C_6$-$C_{16}$ hydrocarbons or hydrocarbons comprising more than 16 carbon atoms and up to 60 carbon atoms, preferably between $C_6$ and $C_{16}$, and in particular alkanes, oils of animal origin, oils of plant origin, glycerides or fluoro oils of synthetic origin, fatty alcohols, fatty acid and/or fatty alcohol esters, non-silicone waxes, and silicones.

For example, the fatty alcohols, fatty esters and fatty acids more particularly contain one or more linear or branched, saturated or unsaturated hydrocarbon-based groups comprising 6 to 60 carbon atoms, which are optionally substituted, in particular with one or more (in particular 1 to 4) hydroxyl groups. If they are unsaturated, these compounds may comprise one to three conjugated or unconjugated carbon-carbon double bonds.

As regards the $C_6$-$C_{16}$ alkanes, they are linear or branched, and possibly cyclic. Examples that may be mentioned include hexane, dodecane and isoparaffins such as isohexadecane, isodecane and isododecane. The linear or branched hydrocarbons containing more than 16 carbon atoms may be chosen from liquid paraffins, petroleum jelly, liquid petroleum jelly, polydecenes, and hydrogenated polyisobutene such as Parleam®.

Among the hydrocarbon-based liquid fatty substances iii) having a global solubility parameter according to the Hansen solubility space of less than or equal to 20 $(MPa)^{1/2}$, mention may be made of oils, which may be chosen from natural or synthetic, hydrocarbon-based, optionally fluorinated, optionally branched oils, alone or as a mixture.

According to a very advantageous embodiment, the dispersion comprises one or more liquid fatty substances which are one or more hydrocarbon-based oils. The hydrocarbon-based oil(s) may be volatile or non-volatile.

According to a preferred embodiment, the liquid hydrocarbon-based oil(s) are hydrocarbon-based oils which are volatile or are a mixture of different volatile oils, more preferentially chosen from isododecane and octyldodecanol.

According to another particular embodiment, the liquid hydrocarbon-based fatty substance(s) iii) are a mixture of a volatile oil and of a non-volatile oil.

Volatile silicone oils that may be mentioned include volatile linear or cyclic silicone oils, notably those with a viscosity ≤8 centistokes (cSt) ($8×10^{-6}$ m$^2$/s), and notably containing from 2 to 10 silicon atoms and in particular from 2 to 7 silicon atoms, these silicones optionally including alkyl or alkoxy groups containing from 1 to 10 carbon atoms. As volatile silicone oils that may be used in the invention, mention may notably be made of dimethicones with viscosities of 5 and 6 cSt, octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

As non-volatile silicone oils, mention may be made of linear or cyclic non-volatile polydimethylsiloxanes (PDMSs); polydimethylsiloxanes including alkyl, alkoxy and/or phenyl groups, which are pendent or at the end of a silicone chain, these groups containing from 2 to 24 carbon atoms; phenyl silicones, for instance phenyl trimethicones, phenyl dimethicones, phenyltrimethylsiloxydiphenylsiloxanes, diphenyl dimethicones, diphenylmethyldiphenyltrisiloxanes and 2-phenylethyl trimethylsiloxysilicates and pentaphenyl silicone oils.

The hydrocarbon-based oil may be chosen from:
hydrocarbon-based oils containing from 8 to 14 carbon atoms, and notably:
branched $C_8$-$C_{14}$ alkanes, for instance $C_8$-$C_{14}$ isoalkanes of petroleum origin (also known as isoparaffins), for instance isododecane (also known as 2,2,4,4,6-pentamethylheptane), isodecane and, for example, the oils sold under the trade names Isopar or Permethyl,
linear alkanes, for instance n-dodecane (C12) and n-tetradecane (C14) sold by Sasol under the respective references Parafol 12-97 and Parafol 14-97, and also mixtures thereof, the undecane-tridecane mixture, the mixtures of n-undecane (C11) and of n-tridecane (C13) obtained in examples 1 and 2 of patent application WO 2008/155059 from the company Cognis, and mixtures thereof,
short-chain esters (containing from 3 to 8 carbon atoms in total) such as ethyl acetate, methyl acetate, propyl acetate or n-butyl acetate,
hydrocarbon-based oils of plant origin such as triglycerides consisting of fatty acid esters of glycerol, the fatty acids of which may have chain lengths ranging from $C_4$ to $C_{24}$, these chains possibly being linear or branched, and saturated or unsaturated; these oils are notably heptanoic acid or octanoic acid triglycerides, or alternatively wheatgerm oil, sunflower oil, grapeseed oil, sesame seed oil, corn oil, apricot oil, castor oil, shea oil, avocado oil, olive oil, soybean oil, sweet almond oil, palm oil, rapeseed oil, cotton oil, hazelnut oil, macadamia oil, jojoba oil, alfalfa oil, poppy oil, pumpkin oil, marrow oil, blackcurrant oil, evening primrose oil, millet oil, barley oil, quinoa oil, rye oil, safflower oil, candlenut oil, passion flower oil or musk rose oil; shea butter; or else caprylic/capric acid triglycerides, for instance those sold by the company Stéarinerie Dubois or those sold under the names Miglyol 810©, 812© and 818© by the company Dynamit Nobel,
synthetic ethers containing from 10 to 40 carbon atoms,
linear or branched hydrocarbons of mineral or synthetic origin, such as petroleum jelly, polydecenes, hydrogenated polyisobutene such as Parleam®, squalane and liquid paraffins, and mixtures thereof;
esters such as oils of formula $R^1C(O)$—O—$R^2$ in which $R^1$ represents a linear or branched fatty acid residue including from 1 to 40 carbon atoms and $R^2$ represents an, in particular branched, hydrocarbon-based chain containing from 1 to 40 carbon atoms, on the condition that $R^1+R^2≥10$, for instance purcellin oil (cetostearyl octanoate), isopropyl myristate, isopropyl palmitate, $C_{12}$ to $C_{15}$ alkyl benzoates, hexyl laurate, diisopropyl adipate, isononyl isononanoate, 2-ethylhexyl palmitate, isostearyl isostearate, 2-hexyldecyl laurate, 2-octyldecyl palmitate, 2-octyldodecyl myristate, alkyl or polyalkyl heptanoates, octanoates, decanoates or ricinoleates such as propylene glycol dioctanoate; hydroxylated esters such as isostearyl lactate, diisostearyl malate and 2-octyldodecyl lactate; polyol esters and pentaerythritol esters, fatty alcohols that are liquid at room temperature, with a branched and/or unsaturated carbon-based chain containing from 12 to 26 carbon atoms, for instance octyldodecanol, isostearyl alcohol, oleyl alcohol, 2-hexyldecanol, 2-butyloctanol and 2-undecylpentadecanol.

In addition to the above, nonlimiting examples of useful hydrophobically modified acrylate film forming copolymers include acrylates/beheneth-25 methacrylate copolymer, acrylates/C10-30 alkyl acrylate crosspolymer, acrylates/ceteth-20 itaconate copolymer, acrylates/ceteth-20 methacrylate copolymer, acrylates/laureth-25 methacrylate copolymer, acrylates/palmeth-20 acrylate copolymer, acrylates/palmeth-25 acrylate copolymer, acrylates/palmeth-25 itaconate copolymer, acrylates/steareth-50 acrylate copolymer, acrylates/steareth-20 itaconate copolymer, acrylates/steareth-20 methacrylate copolymer, acrylates/stearyl methacrylate copolymer, acrylates/vinyl isodecanoate crosspolymer, acrylates/steareth-20 methacrylate crosspolymer, octylacrylamide/acrylates/butylaminoethyl methacrylates copolymer, acrylates/C12-alkylmethacrylate copolymer, acrylates/steareth (or ceteth)-20 itaconate copolymer, steareth-10 allyl ether/acrylate copolymer, acrylates/vinyl acetate crosspolymer, glyceryl polymethacrylate, ammonium acryloyldimethyltaurate/beheneth-25 methacrylate copolymer, and a mixture thereof. A particularly useful hydrophobically modified acrylate film forming copolymer is acrylates/stearyl methacrylate copolymer.

In certain exemplary and non-limiting embodiments, the hydrophobically modified acrylate film forming copolymers are chosen from the copolymers resulting from the polymerization of at least one monomer of formula (II):

$$H_2C=CH(R^1)COOH \quad (II)$$

Formula (II) wherein $R_1$ is chosen from H or $CH_3$ or $C_2H_5$, providing acrylic acid, methacrylic acid, or ethacrylic acid monomers, and at least one monomer of $(C_{10}$-$C_{30})$alkyl ester of unsaturated carboxylic acid type corresponding to the monomer of formula (III):

$$H_2C=CH(R^2)-C(O)-OR^3 \quad (III)$$

Formula (III) wherein $R^2$ is chosen from H or $CH_3$ or $C_2H_5$, providing acrylate, methacrylate or ethacrylate units, $R^3$ denoting a linear or branched $C_{10}$-$C_{30}$ alkyl radical, such as a linear or branched $C_{12}$-$C_{22}$ alkyl radical.

According to another variant of the invention the useful hydrophobically modified acrylate film forming homopolymers resulting from the polymerization of at least one monomer of $(C_{10}$-$C_{30})$alkyl ester of unsaturated carboxylic acid type corresponding to the monomer of formula (III) as defined herein before.

Non-limiting examples of $(C_{10}$-$C_{30})$alkyl esters of unsaturated carboxylic acids are for example chosen from lauryl acrylate, stearyl acrylate, decyl acrylate, isodecyl acrylate, dodecyl acrylate and the corresponding methacrylates, such as lauryl methacrylate, stearyl methacrylate, decyl methacrylate, isodecyl methacrylate and dodecyl methacrylate, and mixtures thereof.

Additionally, crosslinked polymers may be chosen according to further exemplary embodiments. For example, such polymers may be chosen from polymers resulting from the polymerization of a mixture of monomers comprising: acrylic acid, an ester of formula (III) described above, in which $R^2$ is chosen from H or $CH_3$, $R^3$ denoting a linear or branched alkyl radical having from 12 to 22 carbon atoms, and a crosslinking agent, which is a well-known copolymerizable polyethylenic unsaturated monomer, such as diallyl phthalate, allyl (meth)acrylate, divinylbenzene, (poly)ethylene glycol dimethacrylate and methylenebisacrylamide.

By way of example, crosslinked polymers comprising about 60% to about 95% by weight of acrylic acid (hydrophilic unit), about 4% to about 40% by weight of $C_{10}$-$C_{30}$ alkyl acrylate (hydrophobic unit), and about 0% to about 6% by weight of crosslinking polymerizable monomer. In yet further embodiments, the crosslinked polymers may comprise about 96% to about 98% by weight of acrylic acid (hydrophilic unit), about 1% to about 4% by weight of a linear or branched $C_{10}$-$C_{30}$ alkyl acrylate (hydrophobic unit), and about 0.1% to about 0.6% by weight of crosslinking polymerizable monomer, such as those described above.

Such copolymers may be selected, for example, from acrylate/$C_{10}$-$C_{30}$ alkyl acrylate copolymers (INCI name: acrylates/$C_{10}$-30 alkyl acrylate crosspolymer), such as the products sold by Lubrizol under the trade names PEMULEN TR1, PEMULEN TR2, CARBOPOL 1382 and CARBOPOL EDT 2020.

In further embodiments, the hydrophobically-modified acrylate film forming copolymers may be chosen from nonionic homopolymers or copolymers containing ethylenically unsaturated monomers of the ester and/or amide type. Nonlimiting examples include the products sold under the names CYANAMER P250 by the company CYTEC (polyacrylamide), methyl methacrylate/ethylene glycol dimethacrylate copolymers (such as PMMA MBX-8C by the company US COSMETICS), butyl methacrylate/methyl methacrylate copolymers (such as ACRYLOID B66 by the company RHOM HMS), and polymethyl methacrylates (BPA 500 by the company KOBO) may be chosen.

The hydrophobically-modified acrylate film forming copolymers may be associative copolymers such as the product sold under the commercial name: NOVETHIX L-10 POLYMER (INCI name: acrylates/beheneth-25 methacrylate copolymer) sold by LUBRIZOL, the product sold under the commercial name: ACULYN 22 (INCI name: acrylates/steareth-20 methacrylate copolymer) sold by DOW CHEMICAL, the product sold under the commercial name: ACULYN 88 (INCI name: acrylates/steareth-20 methacrylate copolymer) sold by DOW CHEMICAL, the product sold under the commercial name: STRUCTURE 2001 (INCI name: acrylates/steareth-20 itaconate copolymer) sold by AKZO NOBEL, and the product sold under the commercial name: STRUCTURE 3001 (INCI name: acrylates/ceteth-20 itaconate co polymer) sold by AKZO NOBEL.

A particularly useful hydrophobically modified acrylate film forming copolymer is acrylates/stearyl methacrylate copolymer.

Preferably, the hydrophobically-modified acrylate film forming copolymers do not include silicone, i.e., the hydrophobically-modified acrylate film forming copolymers are not hydrophobically-modified silicone acrylate film forming copolymers, e.g., acrylates/dimethicone copolymers. However, in some instances, hydrophobically-modified silicone acrylate film forming copolymers may be used.

The amount of hydrophobically-modified acrylate film forming copolymers in the makeup removing composition can vary but is typically in an amount of about 15 to about 60 wt. % based on the total weight of the makeup removing composition. The amount of hydrophobically-modified acrylate film forming copolymers in the makeup removing composition may be from about 15 to about 55 wt. %, about 15 to about 50 wt. %, about 15 to about 45 wt. %, about 15 to about 40 wt. %, about 15 to about 35 wt. %, about 20 to about 60 wt. %, about 20 to about 55 wt. %, about 20 to about 50 wt. %, about 20 to about 45 wt. %, about 20 to about 40 wt. %, about 20 to about 35 wt. %, about 25 to about 60 wt. %, about 25 to about 55 wt. %, about 25 to about 50 wt. %, about 25 to about 45 wt. %, about 25 to about 40 wt. %, or about 25 to about 35 wt. %, based on the total weight of the makeup removing composition.

Hydrophilic Film Forming Polymer

Hydrophilic film-forming polymers can be water-soluble polymer or water-dispersible. "Water-dispersible" polymers refers to polymers that when exposed to water creates a two-phase system, where one phase contains finely divided polymer particles distributed throughout the second phase, which is water. The particles form the disperse phase.

Nonlimiting examples of hydrophilic film forming polymers include polyurethanes, vinyl polymers, natural polymers, copolymers derived from C4-C8 monounsaturated carboxylic acids or anhydrides, methyl vinyl ether/butyl monomaleate copolymers, polysaccharides, guar gums and modified guar gums, celluloses, gellan gum and derivatives thereof, acrylate and methacrylate copolymers, polyvinyl pyrollidone, polyvinyl alcohol, polyvinyl acetate, water soluble gums, water soluble celluloses, dextrans, hyaluronic acid, cyclodextrins, polysaccharide polymers, polyvinyl caprolactam-polyvinyl acetate-polyethylene glycol graft copolymers, and mixtures thereof.

In some instances, the hydrophilic film-forming polymer may be chosen from polyvinyl pyrollidone (also known as PVP, povidone or copovidone) or a derivative thereof, polyvinyl alcohol, polyvinyl acetate, water soluble gums (e.g., gum arabic, sclerotium gum, xanthan, carrageenan, guar, and derivatives thereof), water soluble celluloses (e.g., hydroxypropylmethylcellulose, hydroxypropylcellulose, hydroxyethylcellulose and the like), dextrans, hyaluronic acid, cyclodextrins, polysaccharide polymers, polyvinyl caprolactam-polyvinyl acetate-polyethylene glycol graft copolymers, and mixtures thereof.

In certain instances, the hydrophilic film-forming polymer is a polyvinyl polymer, for example, polyvinyl pyrollidone, polyvinyl alcohol, polyvinyl acetate, and mixtures thereof. Polyvinyl pyrollidone, polyvinyl alcohol, and mixtures thereof are particularly useful.

The total amount of hydrophilic film-forming polymer in the makeup removing composition can vary but is typically in an amount of about 1 to about 25 wt. %, based on the total weight of the composition. Similarly, total amount of hydrophilic film-forming polymer in the makeup removing composition is about 1 to about 20 wt. %, about 1 to about 15 wt. %, about 1 to about 10 wt. %, about 1 to about 5 wt. %, about 2 to bout 25 wt. %, about 2 to about 20 wt. %, about 2 to about 15 wt. %, about 2 to about 10 wt. %, or about 2 to about 5 wt. %, about 3 to about 25 wt. %, about 3 to about 20 wt. %, about 3 to about 15 wt. %, about 3 to about 10 wt. %, or about 3 to about 6 wt. %, based on the total weight of the composition.

Volatile Oil

The term "volatile oil" is intended to mean an oil that can evaporate on contact with the skin in less than one hour, at ambient temperature (20° C.) and atmospheric pressure (760 mmHg). More specifically, a volatile oil has an evaporation rate ranging from 0.01 to 200 mg/cm$^2$ min. Exemplary volatile oils include hydrocarbon oils, silicone oils, and ester oils.

Nonlimiting examples of suitable hydrocarbon-based oils include volatile hydrocarbon oils having from 8 to 16 carbon atoms and in particular branched $C_8$ to $C_{16}$ alkanes such as $C_8$ to $C_{16}$ isoalkanes (also known as isoparaffins), isododecane, isodecane, isohexadecane, and for example, the oils sold under the trade names of ISOPAR or PERMETHYL, the $C_8$ to $C_{16}$ branched esters such as isohexyl or isodecyl neopentanoate, alcohols, and their mixtures. In some instances, the volatile hydrocarbon-based oils have a flash point of at least 40° C. Non-limiting examples of volatile hydrocarbon-based oils include those set forth in the table below.

| Compound | Flash Point (° C.) |
| --- | --- |
| Isododecane | 43 |
| Isohexadecane | 102 |
| Isodecyl neopentanoate | 118 |
| Propylene glycol n-butyl ether | 60 |
| Ethyl 3-ethoxypropionate | 58 |
| Propylene glycol methylether acetate | 46 |
| isoparaffin $C_{11}$-$C_{13}$ (e.g., ISOPAR L) | 62 |
| isoparaffin $C_{11}$-$C_{12}$ (e.g., ISOPAR H) | 56 |

The volatile oil may also be chosen from volatile silicone oils, which may be linear or cyclic, having a viscosity, at room temperature, of less than or equal to 6 cSt, and having from 2 to 7 silicon atoms, optionally substituted with alkyl or alkoxy groups of 1 to 10 carbon atoms. Non-limiting examples of suitable volatile silicone oils include set forth in the table below.

| Compound | Flash Point (° C.) | Viscosity (cSt) |
| --- | --- | --- |
| Octyltrimethicone | 93 | 1.2 |
| Hexyltrimethicone | 79 | 1.2 |
| Decamethylcyclopentasiloxane (cyclopentasiloxane or D5) | 72 | 4.2 |
| Octamethylcyclotetrasiloxane (cyclotetradimethylsiloxane or D4) | 55 | 2.5 |
| Dodecamethylcyclohexasiloxane (D6) | 93 | 7 |
| Decamethyltetrasiloxane(L4) | 63 | 1.7 |
| KF-96 A from Shin Etsu | 94 | 6 |
| PDMS (polydimethylsiloxane) DC 200 (1.5 cSt) from Dow Corning | 56 | 1.5 |
| PDMS DC 200 (2 cSt) from Dow Corning | 87 | 2 |
| PDMS DC 200 (5 cSt) from Dow Corning | 134 | 5 |
| PDMS DC 200 (3 St) from Dow Corning | 102 | 3 |

Nonlimiting examples of volatile ester oils include ethyl acetate, butyl acetate and isopropyl acetate.

In certain instances, the volatile oil is a hydrocarbon based-based oil. Nonlimiting examples that are particularly useful include isododecane, isodecane, isohexadecane, and mixtures thereof, preferably isododecane.

The total amount of the volatile oil in the makeup removing composition can vary but is typically about 30 to about 75 wt. %, based on the total weight of the makeup removing composition. In some instances, the total amount of volatile oil is about 30 to about 70 wt. %, about 30 to about 65 wt. %, about 35 to about 75 wt. %, about 35 to about 70 wt. %, about 35 to about 65 wt. %, about 40 to about 75 wt. %, about 40 to about 70 wt. %, about 40 to about 65 wt. %, based on the total weight of the makeup removing composition.

The amount of volatile oil in the aqueous makeup removing compositions often differs from the amount of volatile oil in the anhydrous makeup removing. The anhydrous makeup composition has little or no water, resulting in a higher amount of volatile oil being present.

With respect to the aqueous makeup removing compositions, the total amount of volatile oil may be from about 30 to about 60 wt. %, about 30 to about 55 wt. %, about 30 to about 50 wt. %, about 35 to about 60 wt. %, about 35 to about 55 wt. %, about 35 to about 50 wt. %, about 40 to about 60 wt. %, about 40 to about 55 wt. %, or about 40 to about 50 wt. %, based on the total weight of the aqueous makeup removing composition.

With respect to the anhydrous makeup removing composition, the total amount of volatile oil may be from about 45 to about 75 wt. %, about 45 to about 70 wt. %, about 50 to about 75 wt. %, about 50 to about 70 wt. %, about 55 to about 75 wt. %, about 55 to about 70 wt. %, about 60 to about 75 wt. %, or about 60 to about 70 wt. %, based on the total weight of the anhydrous makeup removing composition.

Nonionic Surfactant/Emulsifier

The nonionic surfactants/emulsifiers include surfactants/emulsifier that are useful for forming a water-in-oil emulsion. For example, the nonionic surfactants/emulsifier may be chosen from alkyl polyglucosides; alcohols, alpha-diols, alkylphenols and esters of fatty acids, being ethoxylated, propoxylated or glycerolated (polyglyceryl-2 isostearate); ethoxylated fatty esters; glyceryl esters of fatty acids; fatty alcohol ethoxylates; alkyl phenol ethoxylates; fatty acid alkoxylates; and mixtures thereof. In some instances, polyglycerolated C8-C30 fatty acid esters are particularly useful include those chosen from polyglycerolated esters of C12-C18 fatty acids, in particular lauric, myristic, palmitic, stearic or isostearic acid, having from 2 to 16 mol of glycerol.

Nonlimiting examples of polyglycerolated fatty acid esters include polyglyceryl-2 laurate, polyglyceryl-3 laurate, polyglyceryl-4 laurate, polyglyceryl-5 laurate, polyglyceryl-6 laurate, polyglyceryl-10 laurate; polyglyceryl-2 myristate, polyglyceryl-3 myristate, polyglyceryl-4 myristate, polyglyceryl-5 myristate, polyglyceryl-6 myristate, polyglyceryl-10 myristate; polyglyceryl-2 palmitate, polyglyceryl-3 palmitate, polyglyceryl-6 palmitate, polyglyceryl-10 palmitate, polyglyceryl-2 isostearate, polyglyceryl-3 isostearate, polyglyceryl-4 isostearate, polyglyceryl-5 isostearate, polyglyceryl-6 isostearate, polyglyceryl-10 isostearate; polyglyceryl-2 stearate, polyglyceryl-3 stearate, polyglyceryl-4 stearate, polyglyceryl-5 stearate, polyglyceryl-6 stearate, polyglyceryl-8 stearate, polyglyceryl-10 stearate, and mixtures thereof. In some instances, polyglyceryl-2 isostearate is particularly useful.

The nonionic surfactants/emulsifiers may be chosen from alcohols and alpha-diols, these compounds being polyethoxylated and/or polypropoxylated and/or polyglycerolated, the number of ethylene oxide and/or propylene oxide groups possibly ranging from 2 to 100, and the number of glycerol groups possibly ranging from 2 to 30; these compounds comprising at least one fatty chain comprising from 8 to 30 carbon atoms and especially from 16 to 30 carbon atoms.

Mention is also be made of polyethoxylated fatty amides preferably having from 2 to 30 ethylene oxide units, polyglycerolated fatty amides including on average from 1 to 5, and in particular from 1.5 to 4, glycerol groups; polyoxyethylenated fatty acid esters of sorbitan having preferably from 2 to 40 units of ethylene oxide, fatty acid esters of sucrose, polyoxyalkylenated and preferably polyoxyethylenated fatty acid esters containing from 2 to 150 mol of ethylene oxide, such as oxyethylenated plant oils.

Useful nonionic surfactants/emulsifiers include those of the alkyl(poly)glycoside type, represented especially by the following general formula: $R_1O—(R_2O)_t-(G)_v$, in which: $R_1$ represents a linear or branched alkyl or alkenyl substituent comprising 6 to 24 carbon atoms and especially 8 to 18 carbon atoms, or an alkylphenyl substituent whose linear or branched alkyl substituent comprises 6 to 24 carbon atoms and especially 8 to 18 carbon atoms; $R_2$ represents a linear or branched alkylene substituent comprising 2 to 4 carbon atoms; G represents a sugar unit comprising 5 to 6 carbon atoms; t denotes a value ranging from 0 to 10 and preferably 0 to 4; and v denotes a value ranging from 1 to 15 and preferably 1 to 4. Preferably, the alkyl(poly)glycoside surfactants are compounds of the formula described above in which: $R_1$ denotes a linear or branched, saturated or unsaturated alkyl substituent comprising from 8 to 18 carbon atoms; $R_2$ represents an alkylene substituent comprising 2 to 4 carbon atoms; t denotes a value ranging from 0 to 3 and preferably equal to 0; and G denotes glucose, fructose or galactose, preferably glucose; the degree of polymerization, i.e. the value of v, possibly ranging from 1 to 15 and preferably from 1 to 4; the mean degree of polymerization more particularly being between 1 and 2. The glucoside bonds between the sugar units are generally of 1-6 or 1-4 type and preferably of 1-4 type. In particular, the alkyl(poly) glycoside surfactant may be an alkyl(poly)glucoside surfactant $C_8/C_{16}$ alkyl(poly)glucosides 1,4, and in particular decyl glucosides and caprylyl/capryl glucosides.

Useful nonionic surfactants/emulsifers are chosen from polyoxyethylenated C8-C30 fatty acid esters (preferably C12-C18) of sorbitan, polyethoxylated C8-C30 (preferably C12-18) fatty alcohols, polyglycerolated C8-C30 (preferably C12-C18) fatty acid esters, polyoxyethylenated compounds having preferably from 2 to 30 moles of ethylene oxide, polyglycerolated compounds having preferably from 2 to 16 moles of glycerol; and mixtures thereof.

The polyoxyethylenated C8-C30 fatty alcohols may be chosen from C12-C18 fatty alcohols, in particular polyoxyethylenated lauryl alcohol, cetyl alcohol, myristyl alcohol, and stearyl alcohol having from 2 to 30 mol of ethylene oxide, such as: cetyl alcohol polyoxyethylenated with 2 EO (Ceteth-2) (HLB 5.3) cetyl alcohol polyoxyethylenated with 6 EO (Ceteth-6) (HLB 11.1) cetyl alcohol polyoxyethylenated with 10 EO (Ceteth-10) (HLB 12.9) cetyl alcohol polyoxyethylenated with 20 EO (Ceteth-20) (HLB 15.7) cetyl alcohol polyoxyethylenated with 24 EO (Ceteth-24) (HLB 16.3) lauryl alcohol polyoxyethylenated with 2 EO (Laureth-2) (HLB 6.1) lauryl alcohol polyoxyethylenated with 3 EO (Laureth-3) (HLB 8) lauryl alcohol polyoxyethylenated with 4 EO (Laureth-4) (HLB 9.4) lauryl alcohol polyoxyethylenated with 7 EO (Laureth-7) (HLB 12.3) lauryl alcohol polyoxyethylenated with 9 EO (Laureth-9) (HLB 13.6) lauryl alcohol polyoxyethylenated with 10 EO (Laureth-10) (HLB 13.9) lauryl alcohol polyoxyethylenated with 12 EO (Laureth-12) (HLB 14.6) lauryl alcohol polyoxyethylenated with 21 EO (Laureth-21) (HLB 15.5) lauryl alcohol polyoxyethylenated with 23 EO (Laureth-23) (HLB 16.3) stearyl alcohol polyoxyethylenated with 2 EO (Steareth-2) (HLB 4.9) stearyl alcohol polyoxyethylenated with 10 EO (Steareth-10) (HLB 12.4) stearyl alcohol polyoxyethylenated with 20 EO (Steareth-20) (HLB 15.2) stearyl alcohol polyoxyethylenated with 21 EO (Steareth-21) (HLB 15.5)

The polyoxyethylenated C8-C30 fatty acid esters (preferably C12-C18) of sorbitan may be chosen from polyoxyethylenated esters of C12-C18 fatty acids, in particular lauric, myristic, cetylic or stearic acids, of sorbitan especially containing from 2 to 30 mol of ethylene oxide, such as: polyoxyethylenated sorbitan monolaurate (4 EO) (Polysorbate-21) (HLB 13.3) polyoxyethylenated sorbitan monolaurate (20 EO) (Polysorbate-20) (HLB 16.7) polyoxyethylenated sorbitan monopalmitate (20 EO) (Polysorbate-40) (HLB 15.6) polyoxyethylenated sorbitan monostearate (20 EO) (Polysorbate-60) (HLB 14.9) polyoxyethylenated sorbitan monostearate (4 EO) (Polysorbate-61) (HLB 9.6) polyoxyethylenated sorbitan monooleate (20 EO) (Polysorbate-80) (HLB 15).

The polyglycerolated C8-C30 fatty acid esters, which are particularly preferred, may be chosen from polyglycerolated esters of C12-C18 fatty acids, in particular lauric, myristic, palmitic, stearic or isostearic acid, having from 2 to 16 mol of glycerol, such as: polyglyceryl-2 laurate, polyglyceryl-3 laurate, polyglyceryl-4 laurate, polyglyceryl-5 laurate, polyglyceryl-6 laurate, polyglyceryl-10 laurate; polyglyceryl-2 myristate, polyglyceryl-3 myristate, polyglyceryl-4 myristate, polyglyceryl-5 myristate, polyglyceryl-6 myristate, polyglyceryl-10 myristate; polyglyceryl-2 palmitate, polyglyceryl-3 palmitate, polyglyceryl-6 palmitate, polyglyceryl-10 palmitate; polyglyceryl-2 isostearate, polyglyceryl-3 isostearate, polyglyceryl-4 isostearate, polyglyceryl-5 isostearate, polyglyceryl-6 isostearate, polyglyceryl-10 isostearate; polyglyceryl-2 stearate, polyglyceryl-3 stearate, polyglyceryl-4 stearate, polyglyceryl-5 stearate, polyglyceryl-6 stearate, polyglyceryl-8 stearate, polyglyceryl-10 stearate, and mixtures thereof.

The total amount of nonionic surfactants/emulsifiers can vary but it typically about 0.01 to about 10 wt. %, based on the total weight of the makeup removing composition. In some instances, the total amount of nonionic surfactants/emulsifiers may be from about 0.01 to about 8 wt. %, about 0.01 to about 6 wt. %, about 0.01 to about 5 wt. %, about 0.01 to about 3 wt. %, about 0.1 to about 10 wt. %, about 0.1 to about 8 wt. %, about 0.1 to about 6 wt. %, about 0.1 to about 5 wt. %, about 0.1 to about 3 wt. %, about 0.5 to about 10 wt. %, about 0.5 to about 8 wt. %, about 0.5 to about 6 wt. %, about 0.5 to about 5 wt. %, or about 0.5 to about 3 wt. %, based on the total weight of the makeup removing composition.

Monoalcohols

The makeup removing composition may optionally include one or more monoalcohols having from 2 to 5 carbon atoms. The amount may vary, but in some instance the makeup removing composition include about 0.1 to about 25 wt. %, of the one or more monoalcohols. Similarly, in some instances, the makeup removing compositions include about 0.1 to about 20 wt. %, about 0.1 to about 15 wt. %, about 0.1 to about 10 wt. %, about 0.1 to about 5 wt. %, about 0.5 to about 20 wt. %, about 0.5 to about 15 wt. %, about 0.5 to about 10 wt. %, about 0.5 wt. % to about 5 wt. % of the one or more monoalcohols, based on the total weight of the makeup removing composition.

In some cases, higher amounts of monoalcohols may be used, for example, about 1 to about 25 wt. %, about 1 to about 20 wt. %, about 1 to about 15 wt. %, about 5 to about 25 wt. %, or about 5 to about 20 wt. %, based on the total weight of the makeup removing composition.

Water

The amount of water in the aqueous makeup removing compositions may vary but is typically about 5 to about 45 wt. %, based on the total weight of the composition. In some cases, however, the total amount of water in the aqueous makeup removing compositions is about 10 to about 45 wt. %, about 10 to about 40 wt. %, about 10 to about 35 wt. %, about 10 to about 30 wt. %, about 10 to about 25 wt. %, about 15 to about 45 wt. %, about 15 to about 40 wt. %, about 15 to about 35 wt. %, about 15 to about 30 wt. %, about 15 to about 25 wt. %, about 20 to about 45 wt. %, about 20 to about 40 wt. %, about 20 to about 35 wt. %, or about 20 to about 35 wt. %, based on the total weight of the composition.

The anhydrous makeup removing compositions are preferably free or essentially free from water. Small amounts of water may nonetheless invariably be present. Nonetheless, typically the total amount of water in the anhydrous makeup removing compositions is 2 wt. % or less. The amount of water in the anhydrous makeup removing composition may be 1 wt. % or less, 0.5 wt. % or less, 0.1 wt. % or less. Similarly, the total amount of water in the anhydrous makeup removing compositions may be about 0.0001 to about 2 wt. %, about 0.0001 to about 1 wt. %, about 0.0001 to about 0.5 wt. %, about 0.0001 to about 0.1 wt. %, about 0.001 to about 2 wt. %, about 0.001 to about 1 wt. %, about 0.001 to about 1 wt. %, about 0.001 to about 0.5 wt. %, about 0.001 to about 0.1 wt. %, about 0.01 to about 2 wt. %, about 0.01 to about 1 wt. %, about 0.01 to about 0.5 wt. %, about 0.01 to about 0.1 wt. %, about 0.1 to about 2 wt. %, or about 0.1 to about 1 wt. %, based on the total weight of the composition.

Plasticizers

Plasticizers are added to improve the properties of the makeup removing composition, for example to make it softer and more flexible, to increase its plasticity, etc. Useful plasticizers include phthalate plasticizers, terephthalate plasticizers, benzoate plasticizers, citrate plasticizers, phosphate plasticizers, adipate plasticizers, and mixtures thereof.

Nonlimiting examples of phthalate plasticizers include dioctyl phthalate, diethylhexyl phthalate, diisononyl phthalate, diisodecyl phthalate, dimethyl phthalate, diethyl phthalate, dibutyl phthalate, diheptyl phthalate, dinonyl phthalate, ditridecyl phthalate, and mixtures thereof.

A nonlimiting examples of a terephthalate plasticizer includes dioctyl terephthalate.

Nonlimiting examples of benzoate plasticizers include 2-(2-(2-phenylcarbonyloxy-ethoxy)ethoxy)ethyl benzoate, glyceryl tribenzoate, trimethylolpropane tribenzoate, isononyl benzoate, 1-methyl-2-(2-phenylcarbonyloxypropoxy)ethyl benzoate, 2,2,4-trimethyl-1,3-pentanediol dibenzoate, n-hexyl benzoate, trimethylolpropane tribenzoate and mixtures thereof.

Nonlimiting examples of citrate plasticizers include acetyl tributyl citrate, acetyl triethyl citrate, tributyl citrate, triethyl citrate, and mixtures thereof.

Nonlimiting examples of phosphate plasticizers include tricresyl phosphate, tributyl phosphate, triphenylphosphate, and mixtures thereof.

Nonlimiting examples of adipate plasticizers include bis (2-ethylhexyl)adipate, dimethyl adipate, monomethyl adipate, dioctyl adipate, diisononyl adipate, dibutyl adipate, diethyl phthalate, diisobutyl adipate, diisopropyl adipate, and mixtures thereof.

Nonlimiting examples of useful plasticizers include acetyl tributyl citrate, acetyl triethyl citrate, tributyl citrate, triethyl citrate, dibutyl phthalate, triphenylphosphate, triacetin, trimethyl pentanyl diisobutyrate, triethylhexanoin, sucrose benzoate, dibutyl adipate, diethyl phthalate, diisobutyl adipate, diisopropyl adipate, dipropylene glycol dibenzoate, N-ethyl toluene sulfonamide, ortho- and para-isomers of N-ethyl toluene sulfonamide, N-(2-hydroxypropyl) benzene sulfonamide, N-(n-butyl) benzene sulfonamide, and mixtures thereof.

The plasticizers are particularly useful in the anhydrous compositions, in particular the makeup removing compositions but may also optionally be included in the aqueous composition, in particular, the aqueous makeup removing compositions. The total amount of the plasticizers included in the makeup removing compositions, when present, is about 0.5 to about 15 wt. %, based on the total weight of the composition. Similarly, the total amount of plasticizer in the composition, when present, may be about 0.5 to about 10 wt. %, about 0.5 to about 8 wt. %, about 0.5 to about 6 wt. %, about 1 to about 15 wt. %, about 1 to about 10 wt. %, about 1 to about 8 wt. %, about 1 to about 6 wt. %, about 2 to about 15 wt. %, about 2 to about 10 wt. %, about 2 to about 8 wt. %, about 2 to about 7 wt. %, about 2 to about 6 wt. %, about 3 to about 15 wt. %, about 3 to about 10 wt. %, about 3 to about 8 wt. %, or about 3 to about 6 wt. %, based on the total weight of the composition.

Miscellaneous Ingredients

The makeup removing compositions may optionally include one or more miscellaneous ingredients. Nonlimiting examples include pH adjusters, fragrances, perfumes, colorants (to color the composition), fruit and/or vegetable extracts, thickening agents, surfactant (that are different from the nonionic surfactants/emulsifiers already set forth above) proteins, polymers (that are different from the hydrophobically modified acrylate film forming polymer and the hydrophilic film forming polymers set forth above), preservatives, salts, emollients, fillers, acids (e.g., salicylic acid, citric acid, fumaric acid, sorbic acid, etc.), clays, active ingredients (e.g., anti-aging ingredients, anti-inflammatory agents, caffeine, panthenol, etc.), vitamins, etc.

The total amount of miscellaneous ingredient may vary but, in some instances, the amount of miscellaneous ingredient in the makeup removing compositions is about 0.001 to about 15 wt. %, based on the total weight of the makeup removing composition. The total amount of miscellaneous ingredients may be about 0.01 to about 15 wt. %, about 0.01 to about 10 wt. %, about 0.01 to about 8 wt. %, about 0.01 to about 5 wt. %, about 0.01 to about 3 wt. %, about 0.01 to about 2 wt. %, about 0.1 to about 15 wt. %, about 0.01 to about 10 wt. %, about 0.1 to about 10 wt. %, about 0.1 to about 8 wt. %, about 0.1 to about 5 wt. %, about 0.1 to about 3 wt. %, about 0.1 to about 2 wt. %, about 1 to about 15 wt. %, about 1 to about 10 wt. %, about 1 to about 8 wt. %, about 1 to about 5 wt. %, or about 1 to about 3 wt. %, based on the total weight of the makeup removing composition.

The pH of the makeup removing composition may vary, provided that the pH is safe for cosmetic purposes, i.e, for application to the skin. In some instances, the pH of the makeup removing composition from about 4 to about 8. Similarly, the pH may be from about 4 to about 7, about 4 to about 6, about 5 to about 8, about 5 to about 7, or about 6 to about 8, about 7 to about 8. In some instances, it is preferable that the makeup removing composition have a pH of less than 7, for example, from about 2 to about 6.5, about 3 to about 6.5, about 4 to about 6.5, about 5 to about 6.5, about 2 to about 6, about 3 to about 6, about 3 to about 5, about 4 to about 6.5, about 4 to about 6, about 4 to about 5, about 4.5 to about 6.5, about 4.5 to about 6, or about 4.5 to about 5.5.

Nonlimiting examples of pH adjusters include organic acids, for example, acetic acid, propionic acid, hexanoic acid, cyclopentanepropionic acid, glycolic acid, pyruvic acid, lactic acid, malonic acid, succinic acid, malic acid, maleic acid, fumaric acid, trifluoroacetic acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and mixtures thereof.

The viscosity of the makeup removing compositions (anhydrous and aqueous compositions) before application onto the skin (before being applied to the skin to form a film) can vary. For example, the compositions may have a viscosity of about 5 mPa·s to about 10,000 mPa·s, about 10 mPa·s to about 10,000 mPa·s, about 15 to about 10,000 mPa·s, about 20 mPa·s to 10,000 mPa·s, about 5 mPa·s to 50,000 mPa·s, about 10 mPa·s to 50,000 mPa·s, about 15 mPa·s to 50,000 mPa·s, about 20 mPa·s to 50,000 mPa·s, about 5 to 25,000 mPa·s, about 10 mPa·s to 25,000 mPa·s, about 15 to 25,000 mPa·s, about 20 mPa·s to 25,000 mPa·s, about 5 mPa·s to 10,000 mPa·s, about 10 mPa·s to 10,000 mPa·s, about 15 mPa·s to 10,000 mPa·s, or about 20 to 10,000 mPa·s, about 5 mPa·s to about 5,000 mPa·s, about 10 mPa·s to about 5,000 mPa·s, about 15 mPa·s to about 5,000 mPa·s, about 20 mPa·s to about 5,000 mps, about 5 mPa·s to about 1,000 mPa·s, about 10 mPa·s to about 1,000 mPa·s, about 15 mPa·s to about 1,000 mPa·s, about 20 to about 1,000 mPa·s, about 5 to about 500 mPa·s, about 10 to about 500 mPa·s, about 15 to about 500 mPa·s, about 20 to about 500 mPa·s, or about 5 to about 250 mPa·s at a temperature of 25° C.

In some cases, the anhydrous makeup removing compositions may have viscosity of about 1 mPa·s to about 1000 mPa·s, about 1 mPa·s to about 500 mPa·s, about 1 mPa·s to about 250 mPa·s, about 1 to about 100 mPa·s, about 1 to about 50 mPa·s, about 2 mPa·s to about 1000 mPa·s, about 2 mPa·s to about 500 mPa·s, about 2 mPa·s to about 250 mPa·s, about 2 to about 100 mPa·s, about 2 to about 50 mPa·s, about 5 mPa·s to about 1000 mPa·s, about 5 mPa·s to about 500 mPa·s, about 5 mPa·s to about 250 mPa·s, about 5 to about 100 mPa·s, or about 5 to about 50 mPa·s at a temperature of 25° C.

The viscosity measurements can be carried out, for example, using a Broooksfield viscometer/rheometer using a RV-3 Disk spindle at a speed of 5, 10, 15, and/or 20 rpm or using a Rheomat with an M4 spindle. An RVDV-II+Pro Viscometer with RheocalcT software may be employed for automated instrument control and data acquisition. The test temperature is maintained at 25° C. by using a Brookfield TC-502P Programmable Refrigerated Bath. From its original container, a sample is transferred into a 600 mL beaker and then tested.

The instant disclosure also relates to methods for cleansing and/or removing makeup from the skin. Although the compositions are typically used to remove makeup from the skin, they are not limited to this use. For example, the compositions may be used to clean skin that does not necessarily include makeup. The composition can be used to remove oil, pollutants, dirt, dead skin, etc., from the skin. Accordingly, the compositions of the instant disclosure can be applied to the skin; allowed to remain on the skin for a period (e.g., a period long enough to allow at least part of the volatile solvent to evaporate such that the composition forms a film on the skin); and subsequently removed from the skin, for example, by peeling the film formed from the skin or my cleansing/rinsing the composition from the skin. More specifically, methods of the instant disclosure include:

(i) applying a makeup removing composition according to the instant disclosure (an aqueous or an anhydrous makeup removing composition) to the skin;

(ii) allowing the composition to remain on the skin for a period; and (iii) removing the composition from the skin.

Typically, the makeup removing composition is allowed to remain on the skin for a period long enough to allow the composition to form a film on the skin. As the volatile oil evaporates, the compositions adhere to makeup on the skin (and to skin) and forms a film. The makeup removing compositions usually form a film that can be peeled from the skin within 15 minutes. Therefore, the makeup removing composition may be allowed to remain on the skin for a period of about 15 seconds to about 15 minutes, about 15 seconds to about 10 minutes, about 30 seconds to about 15 minutes, about 30 seconds to about 10 minutes, about 1 minute to about 15 minutes, about 1 minute to about 10 minutes, about 2 minutes to about 15 minutes, or about 2 minutes to about 10 minutes.

After a period of time, as discussed above, the makeup removing composition is removed from the skin, typically peeled from the skin. Makeup from the skin is attached to the makeup removing composition and separates from the skin with the makeup removing composition, which is typically removed after forming a film on the skin. The methods are typically used on skin upon which makeup is commonly applied, for example, the skin of the face. However, the makeup composition can be applied to the skin of other areas of the body (other than face) to cleanse and/or remove makeup from the skin of other parts of the body. As already noted, the film formed by the makeup removing composition can be peeled from the skin. In fact, it can be peeled from the skin in one piece, if desired. The films can be peeled using the fingers to pull the films from the skin. The films remove makeup, oils, pollutants, dead skin, etc., and are useful for providing deep pore cleansing. Although the films formed by the makeup removing compositions are typically removed by peeling, they may also be removed by other means, for example, using cleansing compositions and/or by scrubbing them away from the skin.

Further to the above, the aqueous composition, especially the aqueous makeup removing composition may comprise or consist of:

(a) about 15 to about 55 wt. %, preferably about 18 to about 50 wt. %, more preferably about 20 to about 45 wt. %, of a hydrophobically modified acrylate film forming copolymer, for example, acrylates/beheneth-25 methacrylate copolymer, acrylates/C10-30 alkyl acrylate crosspolymer, acrylates/ceteth-20 itaconate copolymer, acrylates/ceteth-20 methacrylate copolymer, acrylates/laureth-25 methacrylate copolymer, acrylates/palmeth-20 acrylate copolymer, acrylates/palmeth-25 acrylate copolymer, acrylates/palmeth-25 itaconate copolymer, acrylates/steareth-50 acrylate copolymer, acrylates/steareth-20 itaconate copolymer, acrylates/steareth-20 methacrylate copolymer, acrylates/stearyl methacrylate copolymer, acrylates/vinyl isodecanoate crosspolymer, acrylates/steareth-20 methacrylate crosspolymer, octylacrylamide/acrylates/butylaminoethyl methacrylates copolymer, acrylates/C12-alkylmethacrylate copolymer, acrylates/steareth (or ceteth)-20 itaconate copolymer steareth-10 allyl ether/acrylate copolymer, acrylates/vinyl acetate crosspolymer, glyceryl polymethacrylate, ammonium acryloyldimethyltaurate/beheneth-25 methacrylate copolymer, and a mixture thereof, preferably acrylates/stearyl methacrylate copolymer;

(b) about 1 to about 25 wt. %, preferably about 1 to about 15 wt. %, more preferably about 2 to about 10 wt. % of a hydrophilic film forming polymer, for example, chosen from polyurethanes, vinyl polymers, natural polymers, copolymers derived from C4-C monounsaturated carboxylic acids or anhydrides, methyl vinyl ether/butyl monomaleate copolymers, polysaccharides, guar gums and modified guar gums, celluloses, gellan gum and derivatives thereof, acrylate and methacrylate copolymers, polyvinyl pyrollidone, polyvinyl alcohol, polyvinyl acetate, water soluble gums, water soluble celluloses, dextrans, hyaluronic acid, cyclodextrins, polysaccharide polymers, polyvinyl caprolactam-polyvinyl acetate-polyethylene glycol graft copolymers, and mixtures thereof, preferably polyvinyl pyrollidone, polyvinyl alcohol, polyvinyl acetate, and mixtures thereof;

(c) about 30 to about 75 wt. % of a volatile oil, preferably about 35 to about 65 wt. %, more preferably about 30 to about 50 wt. % of a volatile oil, for example, a volatile oil chosen from hydrocarbon oils, silicone oils, ester oils, and a mixture thereof, preferably a hydrocarbon oil, more preferably a hydrocarbon oil chosen from isoparaffin, isohexadecane, isododecane, isodecane, undecane, tridecane, dodecane, isohexyl, isodecyl, neopentanoate, and a mixture thereof;

(d) 0.01 to about 10 wt. % of a nonionic surfactant, preferably about 0.1 to about 8 wt. %, more preferably about 0.5 to about 6 wt. % of a nonionic surfactant for example, a polyglycerolated fatty acid ester;

(e) 0.1 to about 25 wt. %, preferably about 0.5 to about 15 wt. %, more preferably about 1 to about 10 wt. % of one or more monoalcohol having from 2 to 5 carbon atoms, preferably ethanol;

(f) about 5 to about 45 wt. % of water, preferably about 10 to about 35 wt. % water, more preferably about 15 to about 30 wt. % of water; and (g) optionally, about 0.001 to about 15 wt. %, preferably about 0.01 to about 10 wt. %, more preferably about 0.1 to about 5 wt. % of miscellaneous ingredients;

wherein the composition is preferably a water-in-oil emulsion and all weight percentages are based on the total weight of the composition.

Furthermore, the aqueous composition, especially the aqueous makeup removing composition may comprise or consist of:

(a) about 15 to about 55 wt. %, preferably about 18 to about 50 wt. %, more preferably about 20 to about 45 wt. %, of acrylates/stearyl methacrylate copolymer;

(b) about 1 to about 25 wt. %, preferably about 1 to about 15 wt. %, more preferably about 2 to about 10 wt. % of a hydrophilic film forming polymer, for example, chosen from polyurethanes, vinyl polymers, natural polymers, copolymers derived from $C_4$-$C_8$ monounsaturated carboxylic acids or anhydrides, methyl vinyl ether/butyl monomaleate copolymers, polysaccharides, guar gums and modified guar gums, celluloses, gellan gum and derivatives thereof, acrylate and methacrylate copolymers, polyvinyl pyrollidone, polyvinyl alcohol, polyvinyl acetate, water soluble gums, water soluble celluloses, dextrans, hyaluronic acid, cyclodextrins, polysaccharide polymers, polyvinyl caprolactam-polyvinyl acetate-polyethylene glycol graft copolymers, and mixtures thereof, preferably polyvinyl pyrollidone, polyvinyl alcohol, polyvinyl acetate, and mixtures thereof;

(c) about 30 to about 75 wt. % of a volatile oil, preferably about 35 to about 65 wt. %, more preferably about 30 to about 50 wt. % of a volatile oil that is a hydrocarbon oil chosen from isoparaffin, isohexadecane, isododecane, isodecane, undecane, tridecane, dodecane, isohexyl, isodecyl, neopentanoate, and a mixture thereof, preferably isododecane;

(d) 0.01 to about 10 wt. % of a nonionic surfactant, preferably about 0.1 to about 8 wt. %, more preferably about 0.5 to about 6 wt. % of a nonionic surfactant that is a polyglycerolated fatty acid ester chosen from polyglyceryl-2 laurate, polyglyceryl-3 laurate, polyglyceryl-4 laurate, polyglyceryl-5 laurate, polyglyceryl-6 laurate, polyglyceryl-10 laurate; polyglyceryl-2 myristate, polyglyceryl-3 myristate, polyglyceryl-4 myristate, polyglyceryl-5 myristate, polyglyceryl-6 myristate, polyglyceryl-10 myristate; polyglyceryl-2 palmitate, polyglyceryl-3 palmitate, polyglyceryl-6 palmitate, polyglyceryl-10 palmitate; polyglyceryl-2 isostearate, polyglyceryl-3 isostearate, polyglyceryl-4 isostearate, polyglyceryl-5 isostearate, polyglyceryl-6 isostearate, polyglyceryl-10 isostearate; polyglyceryl-2 stearate, polyglyceryl-3 stearate, polyglyceryl-4 stearate, polyglyceryl-5 stearate, polyglyceryl-6 stearate, polyglyceryl-8 stearate, polyglyceryl-10 stearate, and mixtures thereof, preferably polyglyceryl-2 isostearate;

(e) 0.1 to about 25 wt. %, preferably about 0.5 to about 15 wt. %, more preferably about 1 to about 10 wt. % of one or more monoalcohol having from 2 to 5 carbon atoms, preferably ethanol;

(f) about 5 to about 45 wt. % of water, preferably about 10 to about 35 wt. % water, more preferably about 15 to about 30 wt. % of water; and (g) optionally, about 0.001 to about 15 wt. %, preferably about 0.01 to about 10 wt. %, more preferably about 0.1 to about 5 wt. % of miscellaneous ingredients;

wherein the composition is preferably a water-in-oil emulsion and all weight percentages are based on the total weight of the composition.

Further to the above, the anhydrous compositions, preferably the anhydrous makeup removing compositions may comprise or consist of 2 wt. % or less, 1 wt. % or less, or 0.5 wt. % or less of water and:

(a) about 15 to about 55 wt. %, preferably about 18 to about 50 wt. %, more preferably about 20 to about 40 wt. % of a hydrophobically modified acrylate film forming copolymer, for example, acrylates/beheneth-25 methacrylate copolymer, acrylates/C10-30 alkyl acrylate crosspolymer, acrylates/ceteth-20 itaconate copolymer, acrylates/ceteth-20 methacrylate copolymer, acrylates/laureth-25 methacrylate copolymer, acrylates/palmeth-20 acrylate copolymer, acrylates/palmeth-25 acrylate copolymer, acrylates/palmeth-25 itaconate copolymer, acrylates/steareth-50 acrylate copolymer, acrylates/steareth-20 itaconate copolymer, acrylates/steareth-20 methacrylate copolymer, acrylates/stearyl methacrylate copolymer, acrylates/vinyl isodecanoate crosspolymer, acrylates/steareth-20 methacrylate crosspolymer, octylacrylamide/acrylates/butylaminoethyl methacrylates copolymer, acrylates/C12-alkylmethacrylate copolymer, acrylates/steareth (or ceteth)-20 itaconate copolymer, steareth-10 allyl ether/acrylate copolymer, acrylates/vinyl acetate crosspolymer, glyceryl polymethacrylate, ammonium acryloyldimethyltaurate/beheneth-25 methacrylate copolymer, and a mixture thereof, preferably acrylates/stearyl methacrylate copolymer;

(b) about 0.5 to about 15 wt. %, preferably about 1 to about 10 wt. %, more preferably about 1 to about 5 wt. % of a plasticizer, for example, chosen from phthalate plasticizers, terephthalate plasticizers, benzoate plasticizers, citrate plasticizers, phosphate plasticizers, adipate plasticizers, and mixtures thereof, preferably a citrate plasticizer, for example, a citrate plasticizer chosen from acetyl tributyl citrate, acetyl triethyl citrate, tributyl citrate, triethyl citrate, and mixtures thereof;

(c) about 30 to about 75 wt. %, preferably about 40 to about 70 wt. %, more preferably about 55 to about 65 wt. % of a volatile oil, for example, a volatile oil chosen from hydrocarbon oils, silicone oils, ester oils, and a mixture thereof, preferably a hydrocarbon oil, more preferably a hydrocarbon oil chosen from isoparaffin, isohexadecane, isododecane, isodecane, undecane, tridecane, dodecane, isohexyl, isodecyl, neopentanoate, and a mixture thereof; and (d) optionally, about 0.001 to about 15 wt. %, preferably about 0.01 to about 10 wt. %, more preferably about 0.1 to about 5 wt. % of miscellaneous ingredients;

wherein all weight percentages are based on the total weight of the composition.

Furthermore, the anhydrous compositions, preferably the anhydrous makeup removing compositions may comprise or consist of 2 wt. % or less, 1 wt. % or less, or 0.5 wt. % or less of water and:

(a) about 15 to about 55 wt. %, preferably about 18 to about 50 wt. %, more preferably about 20 to about 35 wt. % of acrylates/stearyl methacrylate copolymer;

(b) about 0.5 to about 15 wt. %, preferably about 1 to about 10 wt. %, more preferably about 1 to about 5 wt. % of a plasticizer, for example, chosen from phthalate plasticizers, terephthalate plasticizers, benzoate plasticizers, citrate plasticizers, phosphate plasticizers, adipate plasticizers, and mixtures thereof, preferably a citrate plasticizer, for example, a citrate plasticizer chosen from acetyl tributyl citrate, acetyl triethyl citrate, tributyl citrate, triethyl citrate, and mixtures thereof; (c) about 30 to about 75 wt. %, preferably about 40 to about 70 wt. %, more preferably about 55 to about 65 wt. % of a volatile oil that is a hydrocarbon oil chosen from chosen from isoparaffin, isohexadecane, isododecane, isodecane, undecane, tridecane, dodecane, isohexyl, isodecyl, neopentanoate, and a mixture thereof, preferably isododecane; and
(d) optionally, about 0.001 to about 15 wt. %, preferably about 0.01 to about 10 wt. %, more preferably about 0.1 to about 5 wt. % of miscellaneous ingredients;
wherein all weight percentages are based on the total weight of the composition.

All ingredients positively set forth throughout the instant disclosure may be negatively excluded from the makeup removing compositions. Nonetheless, in some instances the makeup removing compositions are free or essentially from sugar alcohols and derivatives thereof. In some instances, the makeup removing compositions are free or essentially free from glycerol. In some instances, the makeup removing compositions are free from silicones. In some instances, the makeup removing compositions are free from anionic surfactants and/or cationic surfactants. In some instances, the makeup removing compositions are free from silica including, or example, fumed silicas, hydrophobically modified silica, silicone powder, and/or silica silylate. In some instances, the makeup removing compositions are free or essentially from polyamides (and/or polyamide particles), such as polyamide-8. In some cases, the makeup removing compositions are free or essentially free from hydrogenated styrene/isoprene copolymer. In some instances, the makeup removing compositions are free or essentially free from one or more mineral thickening agents, for example, silica silylate, fumed silica, zeolite, natural clay, synthetic clay, kaolin, hectorite, organically modified hectorite (e.g., INCI: pentaerythrityl tetraisostearate (and) disteardimonium hectorite (and) propylene carbonate), an activated clay (e.g., disteardimonium hectorite, stearalkonium hectorite, quaternium-18 bentonite, quaternium-18 hectorite, and benzalkonium bentonite), and a mixture thereof.

Implementation of the present disclosure is provided by way of the following examples. The examples serve to illustrate the technology without being limiting in nature.

Example 1

Aqueous Compositions

Example 2

Anhydrous Compositions

|   |   | Inventive H | Comparative I |
|---|---|---|---|
| (a) | ACRYLATES/STEARYL METHACRYLATE COPOLYMER | 30 | 30 |
| (b) | TRIETHYL CITRATE | 5 | 0 |
| (c) | ISODODECANE | 70 | 65 |
|   | WATER | <1 | <1 |
|   | Viscosity (mPa · s) | 7.1 | 6.4 |
|   | Form | Liquid | Liquid |

Example 3

Comparative Testing

A study was carried out to assess the ability of films formed from the compositions of Examples 1 and 2 to remove makeup. Three commercially available makeup products were used in the testing described below.

1. 10 uL of a commercially available long-wear foundation was spread on the forearm with one finger in a circular motion for ten circular motions and allowed to dry for about 30 minutes. After drying, 1 drop (0.1-0.15 g) of one of the compositions from Examples 1 and 2 was applied in a circular motion for ten circular motions and allowed to dry and form a film. After forming a film, the composition was peeled/rubbed from the skin.

2. A commercially available long-wear lipstick was provided in a pump bottle with an applicator. After pumping the bottle 3 times, the applicator was removed and used to apply the lipstick to the forearm in a circular motion for ten circular motions and allowed to dry for about 30 minutes. After drying, 1 drop (0.1-0.15 g) of one of the compositions from Examples 1 and 2 was applied in a circular motion for ten circular motions and allowed to dry and form a film. After forming a film, the composition was peeled/rubbed from the skin.

|   |   | Inventive | Comparative | | | | | |
|---|---|---|---|---|---|---|---|---|
|   |   | A | B | C | D | E | F | G |
| (a) | Hydrophobically Modified Acrylate Film Former | 24.5 | 24.5 | 10.5 |   |   |   |   |
|   | ACRYLATES COPOLYMER |   |   |   |   |   | 20.1 |   |
|   | CARBOMER |   |   |   | 24.5 |   |   | 7 |
|   | (P)CARBOMER |   |   |   |   | 24.5 |   |   |
| (b) | POLYVINYL ALCOHOL | 3.1 |   | 7.2 | 3.1 | 3.1 | 2.1 | 3.1 |
|   | PVP | 0.5 |   | 1.2 | 0.5 | 0.5 | 0.3 | 0.5 |
| (c) | ISODODECANE | 46.5 | 46.5 | 19.5 | 45.5 | 45.5 | 10 | 63 |
| (d) | POLYGLYCERYL-6 CAPRYLATE |   |   | 1.2 |   | 1.2 | 1.2 |   |
|   | POLYGLYCERYL-2 ISOSTEARATE | 1.2 | 1.2 |   | 1.2 | 1.2 |   | 1.2 |
|   | PEG-8 | 0.9 | 0.9 | 2.1 | 0.9 | 0.9 | 0.6 | 0.9 |
| (e) | ALCOHOL DENAT. | 3 | 3 | 7 | 3 | 3 | 2 | 3 |
|   | WATER | 21.303 | 24.9 | 51.307 | 21.303 | 21.303 | 62.9 | 21.303 |
|   | Form | W/O Emulsion Lotion | W/O Emulsion Lotion | O/W Emulsion Lotion | W/O Emulsion Thick Paste | W/O Emulsion Thick Paste | O/W Emulsion Lotion | W/O Emulsion Thick Paste |

3. A commercially available water-proof mascara was provided in a pump bottle with an applicator. After pumping the pump bottle 3 times, the applicator was removed and used to apply the mascara to the forearm with the applicator. This step was repeated 3 times (for a total of 4 applications of mascara to the forearm) and the mascara was allowed to dry for 30 minutes. After drying, 1 drop (0.1-0.15 g) of one of the compositions from Examples 1 and 2 was applied in a circular motion for ten circular motions and allowed to dry and form a film. After forming a film, the composition was peeled/rubbed from the skin.

Removability was ranked according to below scale.

| 1 | 2 | 3 | 4 | 5 |
|---|---|---|---|---|
| Not removing | Poor | Fair | Good | Very Good |

Film peeling-ability was ranked according to below scale.

| 1 | 2 | 3 | 4 | 5 |
|---|---|---|---|---|
| Not Peel-able | Poor | Fair | Good | Very Good |

Irritation level was ranked according to below scale.

| 1 | 2 | 3 | 4 | 5 |
|---|---|---|---|---|
| No irritation | Slight irritation | Irritation | Strong Irritation | Severe Irritation |

The results for the compositions tested are shown in the following tables.

| Inventive Composition A | | | |
|---|---|---|---|
| | Commercially available long-wear foundation | Commercially available long-wear liquid lipstick | Commercially available water-proof mascara |
| Removability | 5 | 5 | 5 |
| Film peeling-ability | 4 | 5 | 4 |
| Irritation | 1 | 1 | 1 |

| Comparative Composition B | | | |
|---|---|---|---|
| | Commercially available long-wear foundation | Commercially available long-wear liquid lipstick | Commercially available water-proof mascara |
| Removability | 3 | 4 | 3 |
| Film peeling-ability | 2 | 2 | 1 |
| Irritation | 3 | 4 | 4 |

| Comparative Composition C | | | |
|---|---|---|---|
| | Commercially available long-wear foundation | Commercially available long-wear liquid lipstick | Commercially available water-proof mascara |
| Removability | 3 | 3 | 2 |
| Film peeling-ability | 5 | 5 | 5 |
| Irritation | 1 | 1 | 1 |

| Comparative Composition G | | | |
|---|---|---|---|
| | Commercially available long-wear foundation | Commercially available long-wear liquid lipstick | Commercially available water-proof mascara |
| Removability | 2 | 3 | 2 |
| Film peeling-ability | 1 | 1 | 1 |
| Irritation | 2 | 3 | 2 |

The results show that Inventive Composition A provided the best results with respect to all three of "removability," "film-peeling ability," and "irritation." Comparative Composition B provided unacceptable results with respect to "film-peeling ability" and "irritation." Comparative Composition C provided poor results with respect to "removability." Comparative Composition G provided inferior results with respect to all three properties ("removability," "film-peeling ability," and "irritation") compared to Inventive Composition A. Thus, using a hydrophobically modified acrylate film former with a second film former in the compositions of the instant disclosure surprisingly improved all three properties of "removability," "film-peeling ability," and "irritation."

The testing described above was also carried out for the anhydrous compositions of Example 2. The results are provided in the tables below.

| Inventive Composition H | | | |
|---|---|---|---|
| | Commercially available long-wear foundation | Commercially available long-wear liquid lipstick | Commercially available water-proof mascara |
| Removability | 4 | 5 | 5 |
| Film peeling-ability | 4 | 4 | 3 |
| Irritation | 2 | 2 | 2 |

| Comparative Composition I | | | |
|---|---|---|---|
| | Commercially available long-wear foundation | Commercially available long-wear liquid lipstick | Commercially available water-proof mascara |
| Removability | 3 | 4 | 4 |
| Film peeling-ability | 2 | 1 | 1 |
| Irritation | 3 | 4 | 4 |

The results show that including a plasticizer (e.g., triethyl citrate) surprisingly improved all three properties of "removability," "film-peeling ability," and "irritation."

The foregoing description illustrates and describes the invention. The disclosure shows and describes only the preferred embodiments but it should be understood that the invention is capable to use in various other combinations, modifications, and environments and is capable of changes or modifications within the scope of the inventive concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein.

As used herein, the terms "comprising," "having," and "including" (or "comprise," "have," and "include") are used in their open, non-limiting sense. The phrase "consisting essentially of" limits the scope of a claim to the specified materials or steps and those that do not materially affect the basic and novel characteristics of the claimed invention.

The terms "a," "an," and "the" are understood to encompass the plural as well as the singular.

Thus, the term "a mixture thereof" is interchangeable with "mixtures thereof." Throughout the disclosure, the term "a mixture thereof" is used, following a list of elements as shown in the following example where letters A-F represent the elements: "one or more elements selected from the group consisting of A, B, C, D, E, F, or mixtures thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements chosen from A, B, C, D, E, F, and a mixture of any two or more of A, B, C, D, E, and F."

Likewise, the term "a salt thereof" also relates to "salts thereof." Thus, where the disclosure refers to "an element selected from the group consisting of A, B, C, D, E, F, a salt thereof, or mixtures thereof," it indicates that that one or more of A, B, C, D, and F may be included, one or more of a salt of A, a salt of B, a salt of C, a salt of D, a salt of E, and a salt of F may be included, or a mixture of any two of A, B, C, D, E, F, a salt of A, a salt of B, a salt of C, a salt of D, a salt of E, and a salt of F may be included.

The salts referred to throughout the disclosure may include salts having a counterion such as an alkali metal, alkaline earth metal, or ammonium counterion. This list of counterions, however, is non-limiting.

The expression "one or more" means "at least one" and thus includes individual components as well as mixtures/combinations.

The term "plurality" means "more than one" or "two or more."

Some of the various categories of components identified for the makeup removing compositions may overlap. In such cases where overlap may exist and the composition/product includes two overlapping components (or more than two overlapping components), an overlapping component does not represent more than one component. For example, a fatty acid may be defined as both a "fatty compound" and a "surfactant/emulsifier." If a particular composition/product includes both a fatty compound component and an emulsifier component, a single fatty acid can serve as only a fatty compound or a surfactant/emulsifier (a single fatty acid does not serve as both the fatty compound and the surfactant/emulsifier).

All percentages, parts and ratios herein are based upon the total weight of the compositions of the present invention, unless otherwise indicated.

All ranges and values disclosed herein are inclusive and combinable. For examples, any value or point described herein that falls within a range described herein can serve as a minimum or maximum value to derive a sub-range, etc. Furthermore, all ranges provided are meant to include every specific range within, and combination of sub-ranges between, the given ranges. Thus, a range from 1-5, includes specifically points 1, 2, 3, 4 and 5, as well as sub-ranges such as 2-5, 3-5, 2-3, 2-4, 1-4, etc.; and points of 1, 2, 3, 4, and 5 includes ranges and sub-ranges of 1-5, 2-5, 3-5, 2-3, 2-4, 1-4, etc.

Other than in the operating examples, or where otherwise indicated, all numbers expressing quantities of ingredients and/or reaction conditions are understood to be modified by "about," whether or not expressly stated. Additionally, all numbers are intended to represent exact figures as additional embodiments, whether or not modified by "about." For example, "an amount of about 1%" includes an amount of exactly 1%. As a further example, "an amount of 1%" includes an amount of about 1%. The term "about" is generally understood to encompass a range of +/−10% from the stated number, and is intended to cover amounts of +/−1%, 2%, 3%, 4%, 5%, 6%, 7%, 8%, 9%, and 10%.

The term "surfactants" includes salts of the surfactants even if not explicitly stated. In other words, whenever the disclosure refers to a surfactant, it is intended that salts of the surfactant are also encompassed to the extent such salts exist, even though the specification may not specifically refer to a salt (or may not refer to a salt in every instance throughout the disclosure), for example, by using language such as "a salt thereof" or "salts thereof." Sodium and potassium are common cations that form salts with surfactants. However, additional cations such as ammonium ions, or alkanolammonium ions such as monoethanolammonium or triethanolammonium ions, may also form salts of surfactants.

The term "substantially free" or "essentially free" as used herein means the specific material may be present in small amounts that do not materially affect the basic and novel characteristics of the claimed invention. For instance, there may be less than 2% by weight of a specific material added to a composition, based on the total weight of the compositions (provided that an amount of less than 2% by weight does not materially affect the basic and novel characteristics of the claimed invention. Similarly, the compositions may include less than 2 wt %, less than 1.5 wt %, less than 1 wt %, less than 0.5 wt %, less than 0.1 wt %, less than 0.05 wt %, or less than 0.01 wt %, or none of the specified material. The term "substantially free" or "essentially free" as used herein may also mean that the specific material is not added to the composition but may still be present in a raw material that is included in the composition.

Furthermore, all components that are positively set forth in the instant disclosure may be negatively excluded from the claims, e.g., a claimed composition may be "free," "essentially free" (or "substantially free") of one or more components that are positively set forth in the instant disclosure.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:

1. An aqueous makeup removing composition comprising:
   (a) about 20 to about 35 wt. % of acrylates/stearyl methacrylate copolymer;
   (b) about 2 to about 10 wt. % of a hydrophilic film forming polymer selected from polyvinyl pyrrolidone, polyvinyl alcohol, polyvinyl acetate, or mixtures thereof;
   (c) about 40 to about 60 wt. % a volatile hydrocarbon oil;
   (d) about 0.5 to about 6 wt. % of a nonionic surfactant selected from polyglycerolated fatty acid esters;
   (e) about 0.1 to about 5 wt. % of a monoalcohol having from 2 to 5 carbon atoms; and
   (f) about 10 to about 25 wt. % of water;
      wherein the composition is a water-in-oil emulsion, and all weight percentages are based on a total weight of the composition.

2. The composition of claim 1, wherein the acrylates/stearyl methacrylate copolymer of (a) is in an amount of about 25 to about 35 wt. %, based on the total weight of the composition.

3. The composition of claim 1, wherein the volatile hydrocarbon oil is selected from isoparaffin, isohexadecane, isododecane, isodecane, undecane, tridecane, dodecane, isohexyl, isodecyl, neopentanoate, or mixtures thereof.

4. An aqueous makeup removing composition comprising:
   (a) about 20 to about 35 wt. % of acrylates/stearyl methacrylate copolymer;
   (b) about 2 to about 10 wt. % of a mixture of polyvinyl pyrrolidone and polyvinyl alcohol;
   (c) about 40 to about 60 wt. % a volatile hydrocarbon oil;
   (d) about 0.5 to about 6 wt. % of a nonionic surfactant selected from polyglycerolated fatty acid esters;
   (e) about 0.1 to about 5 wt. % of ethanol; and
   (f) about 10 to about 25 wt. % of water;
      wherein the composition is a water-in-oil emulsion, and all weight percentages are based on a total weight of the composition.

5. The composition of claim 4, wherein the acrylates/stearyl methacrylate copolymer of (a) is in an amount of about 25 to about 35 wt. %, based on the total weight of the composition.

6. The composition of claim 4, wherein the volatile hydrocarbon oil is selected from isoparaffin, isohexadecane, isododecane, isodecane, undecane, tridecane, dodecane, isohexyl, isodecyl, neopentanoate, or mixtures thereof.

7. The composition of claim 4, wherein the volatile hydrocarbon oil is isododecane.

8. A method for removing makeup from skin comprising:
   (i) applying the aqueous makeup removing composition of claim 1 to the skin;
   (ii) allowing the composition to remain on the skin for a period; and
   (iii) removing the composition from the skin after the period.

9. The method of claim 8, wherein the composition forms a film on the skin.

10. A method for removing makeup from skin comprising:
    (i) applying the aqueous makeup removing composition of claim 4 to the skin;
    (ii) allowing the composition to remain on the skin for a period; and
    (iii) removing the composition from the skin after the period.

11. The method of claim 10, wherein the composition forms a film on the skin.

* * * * *